US005833654A

United States Patent [19]
Powers et al.

[11] Patent Number: 5,833,654
[45] Date of Patent: Nov. 10, 1998

[54] LONGITUDINALLY ALIGNED DUAL RESERVOIR ACCESS PORT

[75] Inventors: Kelly B. Powers, North Salt Lake, Utah; Kelly J. Christian, Livermore, Calif.; Kenneth A. Eliasen, West Jordan, Utah; Mel Rosenblatt, New Haven, Conn.

[73] Assignee: C. R. Bard, Inc., Murray Hill, N.J.

[21] Appl. No.: 784,580

[22] Filed: Jan. 17, 1997

[51] Int. Cl.⁶ .................................................. A61M 11/00
[52] U.S. Cl. ............................................. 604/93; 604/175
[58] Field of Search ................................ 604/93, 174, 175, 604/116, 280, 905

[56] References Cited

U.S. PATENT DOCUMENTS

| | | | |
|---|---|---|---|
| 4,692,146 | 9/1987 | Hilger | 604/93 |
| 4,695,273 | 9/1987 | Brown | 604/173 |
| 4,892,518 | 1/1990 | Cupp et al. | 604/93 |
| 5,084,015 | 1/1992 | Moriuchi | 64/93 |
| 5,213,574 | 5/1993 | Tucker | 604/93 |
| 5,360,407 | 11/1994 | Leonard | 604/175 |
| 5,387,192 | 2/1995 | Glantz et al. | 604/93 |
| 5,395,324 | 3/1995 | Hinrichs et al. | 604/86 |
| 5,421,814 | 6/1995 | Geary | 604/4 |
| 5,558,641 | 9/1996 | Glantz et al. | 604/93 |
| 5,562,617 | 10/1996 | Finch, Jr. et al. | 604/93 |
| 5,562,618 | 10/1996 | Cai et al. | 64/93 |
| 5,632,729 | 5/1997 | Cai et al. | 604/93 |

*Primary Examiner*—John D. Yasko
*Attorney, Agent, or Firm*—Trask, Britt & Rossa

[57] ABSTRACT

A dual reservoir access port includes a metal casing having a top surface with recessed, open proximal and distal fluid reservoirs. Projecting from the casing on the side of the distal fluid reservoir opposite from the proximal fluid reservoir is a dual prong metal outlet stem. The distal fluid reservoir is carried within an open-topped basket that is disposed in a cup formed in the top surface of the casing. A first fluid flow pathway extends from the proximal fluid reservoir, between the basket and the wall of the distal cup, to the outlet stem. A second fluid flow pathway extends directly from the distal fluid reservoir to the outlet stem. A needle-penetrable compound septum is disposed against the casing simultaneously closing the top of the proximal fluid reservoir and the top of the distal fluid reservoir. A plastic jacket clamps the septum against the casing and compresses the periphery of the septum to effect a fluid seal by the septum of each of the fluid reservoirs. An annular sleeve mechanically locks and fluid couples a dual lumen catheter to the outlet stem. The catheter may be chosen from among three dual lumen catheters, each having a combination of material composition and lumen configuration that is distinct from those of the others of the catheters.

120 Claims, 16 Drawing Sheets

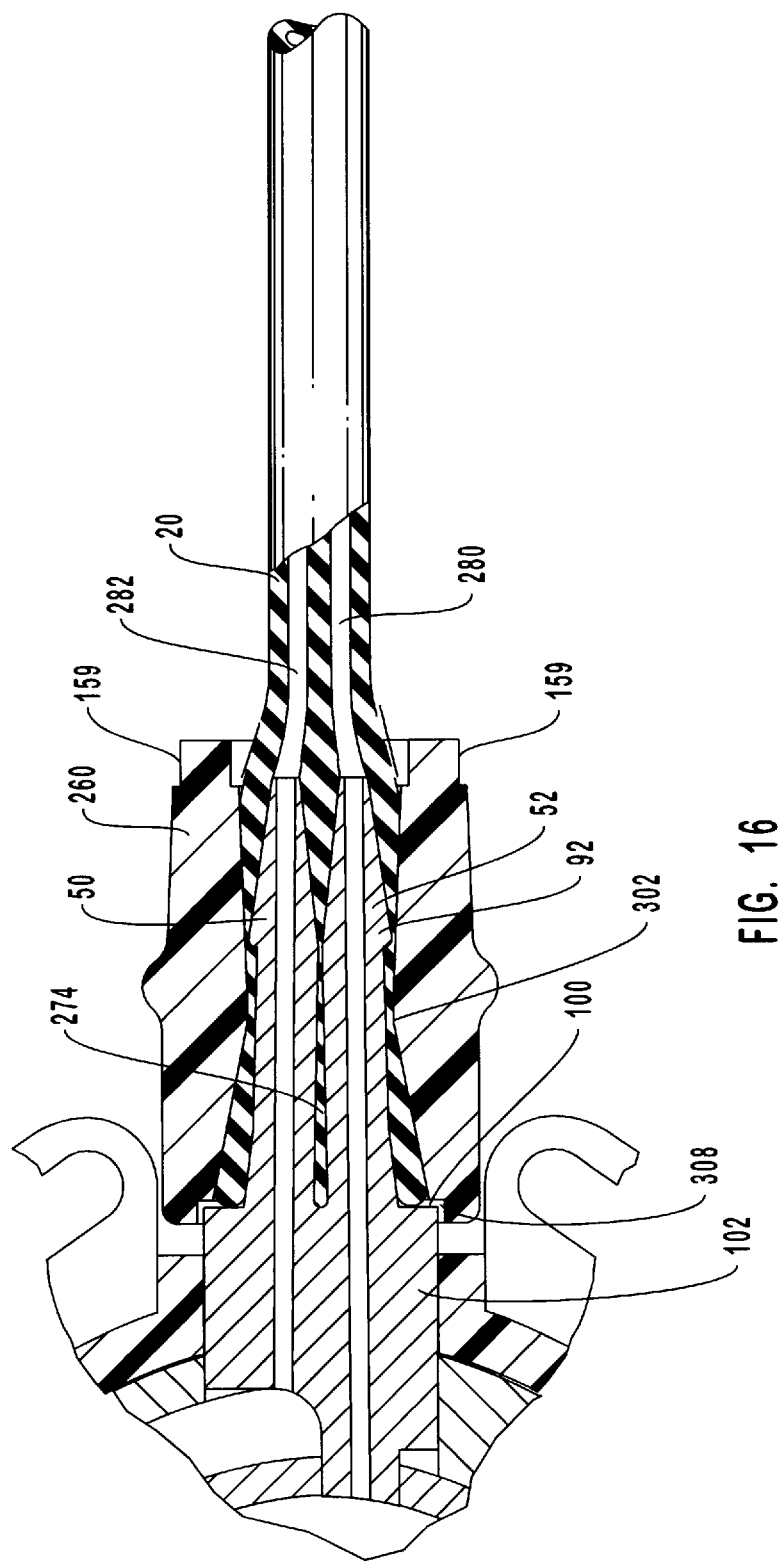

LONGITUDINALLY ALIGNED DUAL RESERVOIR ACCESS PORT

BACKGROUND OF THE INVENTION

1. Field of the Invention

The present invention relates to implantable access ports and, more specifically, to dual reservoir vascular access ports.

2. Background Art

Implantable vascular access systems are used extensively in the medical field to facilitate the performance of recurrent therapeutic tasks inside the body of a patient. Such a vascular access system generally comprises an implantable access port attached to the proximal end of a catheter. A typical access port comprises a needle-impenetrable housing having a fluid reservoir that is sealed by a needle penetrable septum. The access port also includes an outlet stem which projects from the housing and endures a fluid passageway that communicates with the fluid reservoir. The outlet stem is used to couple the catheter to the housing.

In use, the entirety of the catheter with the access port attached thereto is implanted at an appropriate location in the tissue of the patient. The distal end of the catheter is disposed at a predetermined location where therapeutic activity is to be affected. Once the vascular access system is implanted, a needle attached to a syringe can selectively access the reservoir of the access port by penetrating the skin of the implantation site for the access port and then the septum. The needle and syringe can then be used to deliver to the reservoir medication or other fluids, which then travel through the outlet stem and catheter to be disposed in the body at the distal end of the catheter. Alternatively, the syringe can be used in aspiration to withdraw bodily fluids located at the distal end of the catheter.

Many access ports in use contain a single fluid reservoir through which medication can be delivered to a patient. Such structures can, however, be severely limiting to medical practitioners. For example, it is often desirable to deliver medicaments to separate locations within the body of a patient, or to deliver such medicaments as are incompatible, if mixed together in a single fluid reservoir before being infused into the body of the patient. Alternatively, it may be desirable to simultaneously deliver the medication to a patient and withdraw blood samples for testing. Such plural functions cannot be performed through the use of a single reservoir access port.

Instead, toward that end, dual reservoir access ports have been developed. Dual reservoir access ports typically comprise a housing having a pair of separate reservoirs formed therein. Each of the fluid reservoirs has a corresponding access opening that is sealed by a discrete septum plug. The septum plugs are secured in place by a jacket that engages the housing.

An outlet stem housing a pair of fluid passageways projects from the exterior of the housing, usually at a between the pair of fluid reservoirs. This causes the fluid reservoirs to be spaced relatively far apart, increasing the overall size of the access port.

Another problem with conventional dual reservoir access ports relates to the method by which access ports are implanted. To do so, a subcutaneous pocket is first created to receive and house the access port. This is done by making an incision in the skin of the patient at the intended implantation site for the access port. The access port is then inserted beneath the skin through the incision.

The outlet stem of the access port must, however, always be received within the pocket last, after the rest of the access port. Only by so doing can a catheter be coupled to the outlet stem of the access port. The outlet stems of most dual reservoir access ports project from a longitudinal side of the housing, between the fluid reservoirs. To implant such access ports, an incision must be made at the implantation site that is at least as long as the access port. Only in this way can the access port be received through the incision followed by the outlet stem. The longer the incision, the longer the healing process before the access port can be freely utilized and the greater the potential for infection or other complications.

An additional shortcoming of the conventional dual reservoir access ports is their inability to be coupled with a variety of different types of catheters. The catheter is typically attached to the access port by sliding the stem of the access port within the lumen of the catheter. A locking sleeve is then slid over the catheter having the stem received therein producing an effective seal between the outlet stem and the catheter.

Conventional dual reservoir access ports can only be coupled with a corresponding catheter made of a defined material having a defined lumen configuration. Such a limitation precludes the medical practitioner from using a desired catheter based on the patient's needs rather than the access port used.

OBJECTS AND SUMMARY OF THE INVENTION

It is an object of the present invention to provide an improved dual reservoir vascular access port.

Another object of the present invention is to provide such an access port having the same fluid capacity as a conventional dual reservoir access port, but being smaller in size than such an access port.

An additional object of the present invention is to provide a dual reservoir access port that can be implanted in small tissue areas in the body of a patient, and can also be used with small children and infants.

Yet another object of the present invention is to provide a dual reservoir access port that can be implanted subcutaneously through a small incision in the skin of the patient.

Finally, it is an object of the present invention to provide a dual reservoir access port that can be selectively attached to dual lumen catheters made of different materials or having different lumen configurations.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, an implantable delivery system is provided. The system includes an implantable dual reservoir access port. The access port comprises a housing having a floor with an encircling sidewall upstanding therefrom.

A proximal fluid reservoir is formed in a proximal end of the housing and communicates with the exterior of the housing through a proximal access aperture. Likewise, a distal fluid reservoir is formed in a distal end of the housing and communicating with the exterior of the housing through a distal access aperture.

The housing further includes a first fluid flow pathway formed in the sidewall of the housing. The first fluid flow pathway extends between the proximal fluid reservoir and a predetermined outlet location at the distal end of the housing. In addition, a second fluid flow pathway extends between the distal fluid reservoir and the predetermined outlet location.

Projecting from the housing at the outlet location is an outlet stem having a free distal end. The outlet stem includes a first and second outlet prong at the distal end of the outlet stem. Each of the first and second outlet prongs has an exterior surface and an inner face. The opposing inner faces define a slot in the distal end of the outlet stem.

The outlet stem also includes a first fluid duct and a second fluid duct. The first fluid duct extends longitudinally through the first outlet prong of the outlet stein to the first fluid flow pathway. The second fluid duct extends longitudinally through the second outlet prong of the outlet stein to the second fluid flow pathway.

A needle-penetrable compound septum overlies the proximal access aperture and the distal access aperture. The compound septum comprises a septum web having a top surface and a bottom surface. Located on the bottom surface is a pair of plugs that are received within a corresponding one of the access apertures. Located on the top surface of the septum web is a pair of needle target domes that are individually aligned with a corresponding one of the plugs.

The access port also includes a clamp configured to compress and secure the septum to the housing. The clamp includes a shoe having an interior surface configured to receive the floor of the housing. The clamp also includes a cap having a pair of apertures formed therethrough. The cap is configured to receive the compound septum and the housing, so that the needle target domes are received within the apertures of the cap. The cap then engages the shoe, compressing the septum against the housing and sealing the access apertures of the housing.

The fluid delivery system also includes a dual lumen catheter that is selectively attached to the outlet stem. The dual lumen catheter can be made of polyurethane or silicone and can have either D-shaped or trapezoidal shaped lumens.

Finally, a locking sleeve is used to secure the dual lumen catheter to the outlet stein. The locking sleeve comprises a proximal end, a distal end, and an interior surface defining a passageway longitudinally extending therethrough. The interior surface of the locking sleeve radially, inwardly compresses a portion of the body wall of the dual lumen catheter against a portion of the exterior surface of the stem. This is accomplished when the distal end of each of the first and second outlet prongs is individually received in a corresponding one of the lumens of the dual-lumen catheter and the dual lumen catheter with the stem received therein is positioned within the passageway of the locking sleeve.

The inventive fluid delivery system has a variety of unique benefits. For example, by positioning the outlet stem at the distal end of the housing, the reservoirs are longitudinally aligned with respect to the outlet stem. In such a configuration, the access port can be advanced longitudinally into a subcutaneous pocket at the implantation site. As a result, the incision at the implantation site need only be so long as to receive the width, rather than the length, of the access port.

Furthermore, the use of a unitary compound septum permits the fluid reservoirs of the device to be positioned close together, decreasing the size of the access port. By minimizing the size of the access port, the access port can be implanted in previously non-conventional implantation sites in the arm of an adult patient, or even be used with small children and infants.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 16 is a cross-sectional top view of the catheter attached to the access port shown in FIG. 15.

DETAILED DESCRIPTION OF THE ILLUSTRATED EMBODIMENTS

Figure 1:
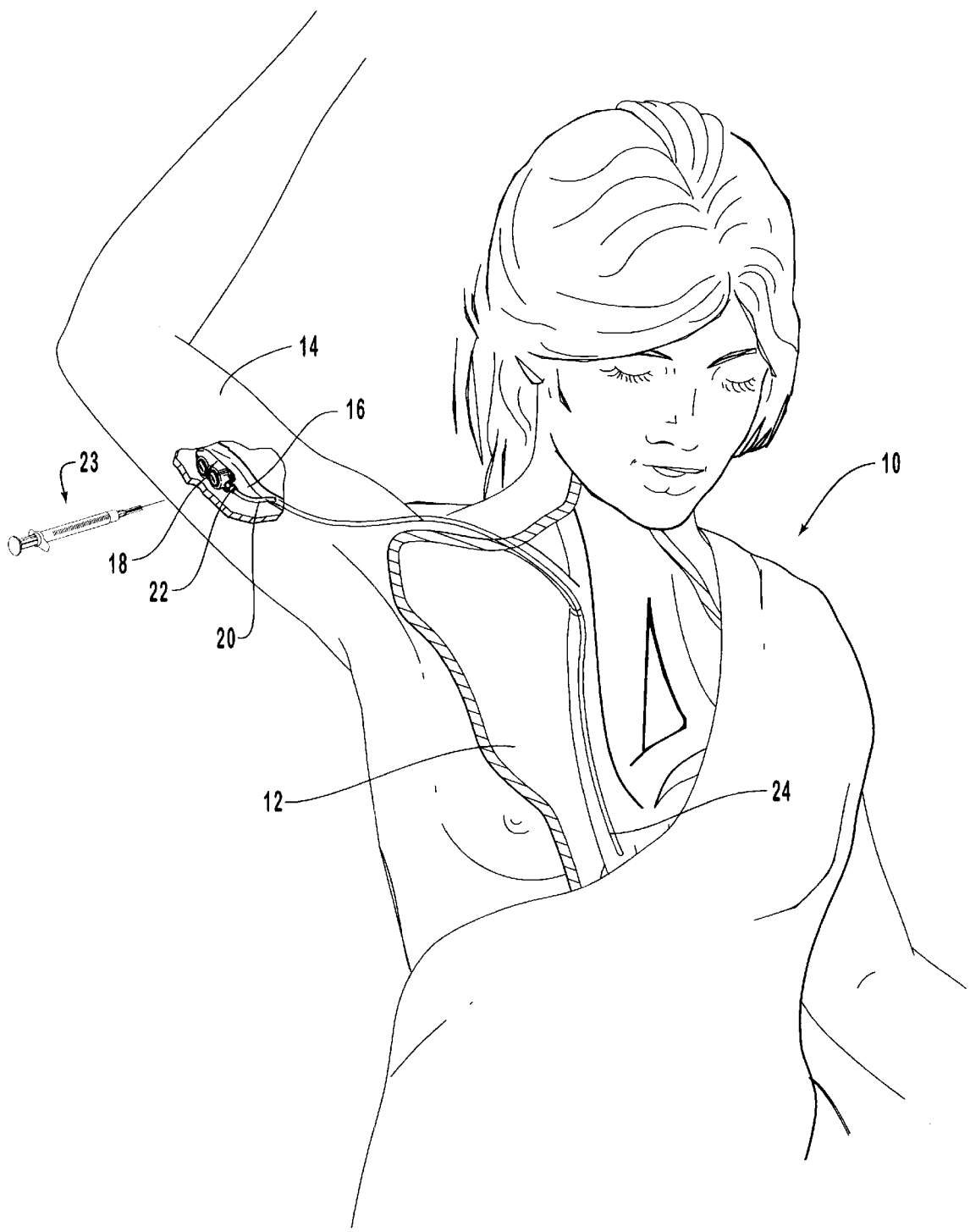
FIG. 1 is a perspective view of a longitudinally aligned dual reservoir access port implanted within the upper arm of a patient and having a catheter attached thereto with an opposing end fed within the vascular system of the patient.

Referring to FIG. 1, a patient 10 is shown having a chest 12 with an arm 14 raised therefrom. A vein 16 extends through arm 14 into chest 12. Subcutaneously implanted at the inside of arm 14 is one embodiment of a longitudinally aligned dual reservoir access port 18 incorporating features of the present invention. Also implanted with access port 18 is an elongated, pliable dual lumen catheter 20 that is coupled thereto. Catheter 20 enters vein 16 in arm 14 and extends therein into chest 12 of patient 10.

Catheter 20 is shown as having a proximal end 22 that is attached in fluid communication with access port 18. Catheter 20 has a distal end 24 that has been advanced within vein 16 to a desired location within chest 12.

The needle of a syringe 23 can be used to transcutaneously deliver medication to either of the fluid reservoirs in access port 18. In turn, the medication travels through catheter 20 and is eventually discharged within the body of patient 10 at distal end 24 of catheter 20.

Alternatively, the needle syringe 23 can be received within access port 18 to aspirate fluid samples. Bodily fluids located at distal end 24 of catheter 20 are drawn into and though catheter 20 to access port 18, and then into syringe 23.

Figure 2:
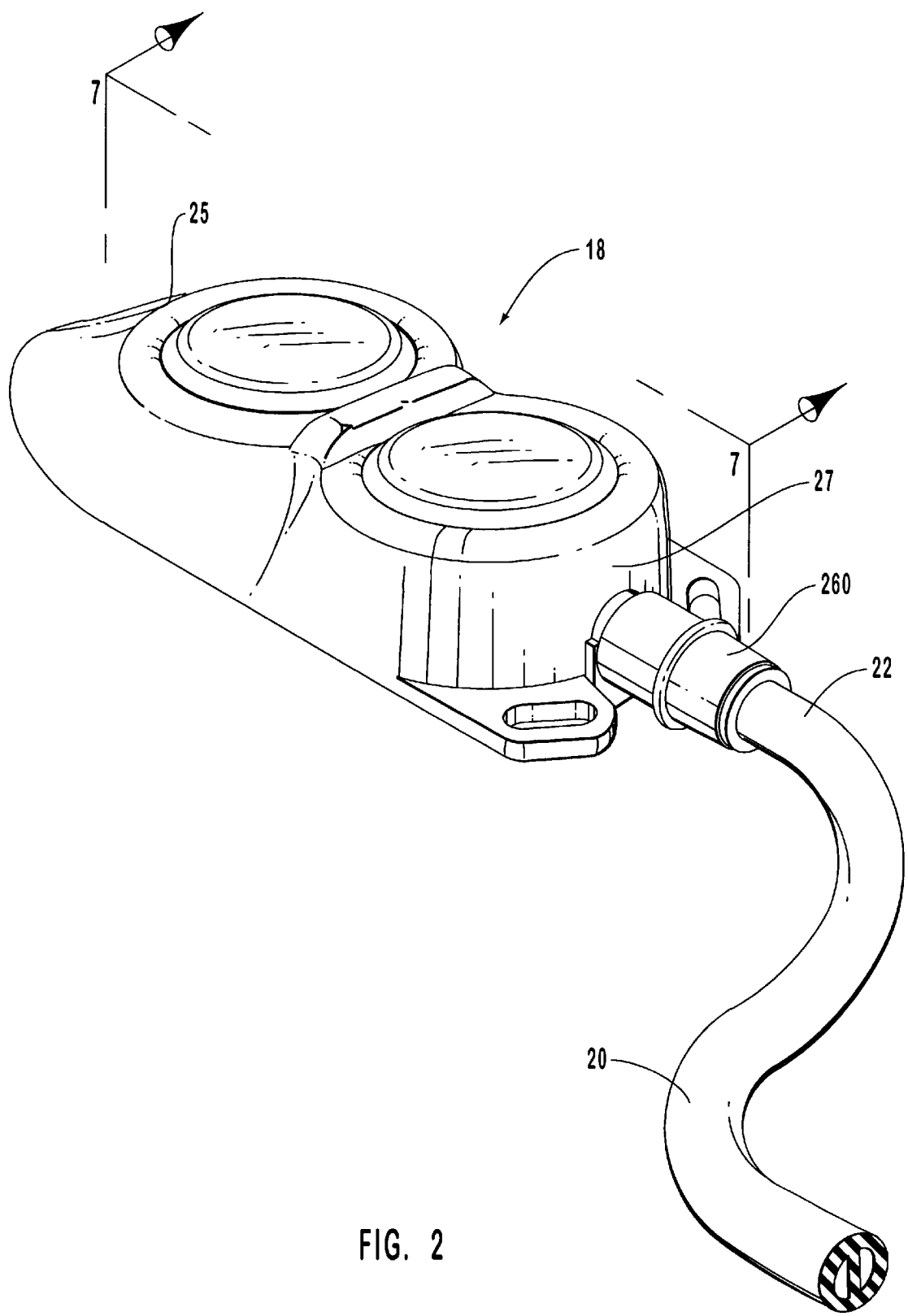
FIG. 2 is an enlarged perspective view of the access port shown in FIG. 1.

Depicted in FIG. 2 is an enlarged perspective view of access port 18 shown in FIG. 1. Access port 18 is shown as having a proximal end 25 and an opposing distal end 27. As will be discussed later in greater detail, proximal end 22 of catheter 20 is attached in fluid communication to distal end 27 of access port 18 by a locking sleeve 260. To better appreciate the internal structure of access port 18, reference is now made to FIG. 3, which shows an exploded view of the elements of access port 18.

Figure 3:
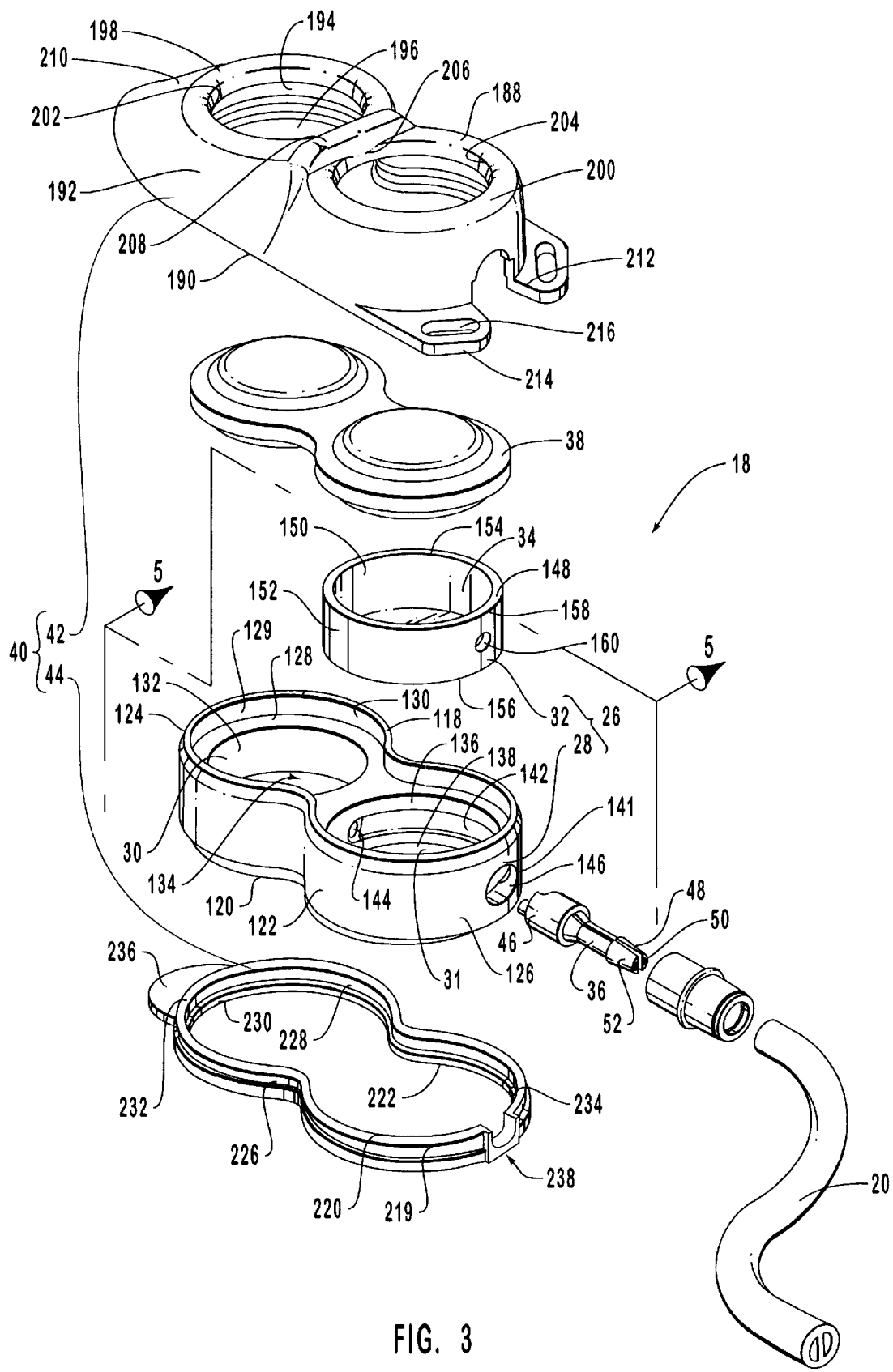
FIG. 3 is a perspective view of the access port shown in FIG. 2 in a disassembled condition.

As depicted in FIG. 3, access port 18 includes a rigid housing 26 which comprises a casing 28 and an open-topped basket 32. Casing 28 has a proximal fluid reservoir 30 and an opposing distal cup 31. Distal cup 31 is configured to receive open-topped basket 32 which in turn defines a distal fluid reservoir 34. An outlet stem 36 is connected to housing 26 to enable fluid coupling to both proximal fluid reservoir 30 and distal fluid reservoir 34.

Access port 18 further includes a compound septum 38 that is secured against housing 26 to cover proximal fluid reservoir 30 and distal fluid reservoir 34. Compound septum 38 is formed of a elastomeric, needle-penetrable material which enables selective needle access to either of reservoirs 30 or 34. A clamp 40, comprising a cap 42 and a shoe 44, is used to compress and secure compound septum 38 against housing 26.

Figure 4A:
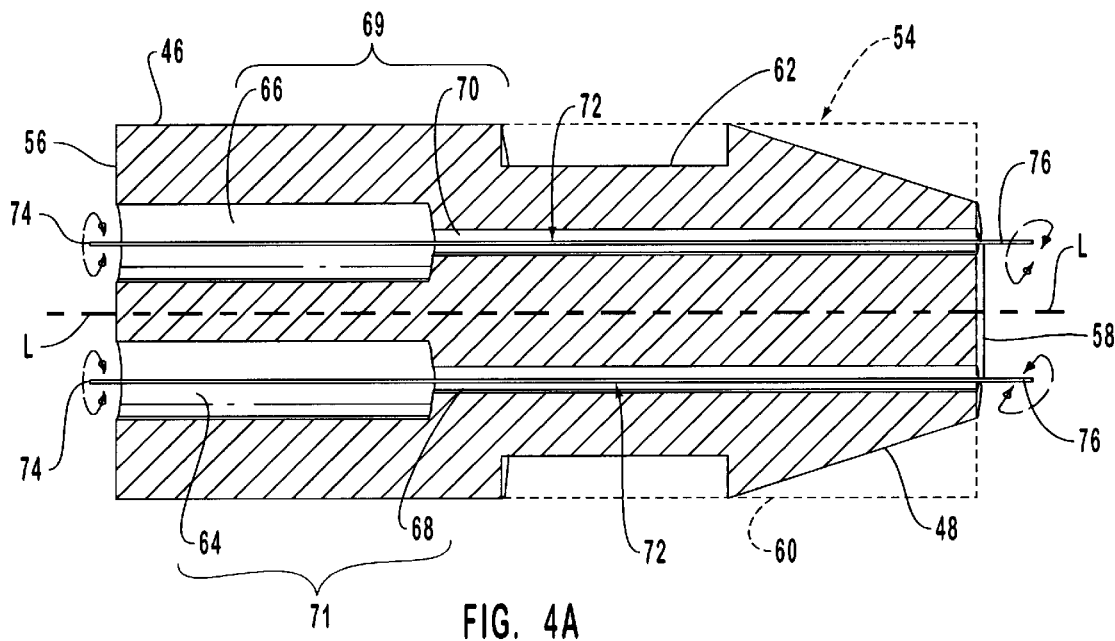
FIGS. 4A–4C are longitudinal cross-sectional plan views showing sequential steps in the manufacture of the outlet stem for the access port shown in FIG. 3.

Outlet stem 36 has a proximal end 46 and an opposing distal end 48. Formed at distal end 48 are a pair of adjacent prongs 50 and 52. As depicted in FIG. 4A, outlet stem 18 is manufactured from a substantially cylindrical stem body 54 having a longitudinal axis L, a proximal end face 56, a distal end face 58, and an encircling exterior surface 60 extending therebetween Using a lathe or other comparable process, an annular groove 62 is formed around exterior surface 60 between proximal end 46 and distal end 48. Likewise, distal end 48 is tapered so as to have a substantially frustoconical shape.

Next, a pair of parallel large pilot holes 64 and 66 are drilled from proximal end face 56 a distance into stem body 54. Likewise, a pair of smaller parallel pilot holes 68 and 70 are drilled from distal end face 58 so as to meet large pilot holes 64 and 66. The intersection of large pilot holes 64 and 66 with smaller pilot holes 68 and 70 forms passageways 69 and 71 that extend longitudinally through stem body 54.

A conventional wire electrostatic discharge machine (hereinafter "a wire EDM") is then used to reconfigure the interior surface of passageways 69 and 71. To do so, an EDM wire 72 of a wire EDM is positioned extending through each of passageways 69 and 71. Each EDM wire 72 has a proximal end 74 positioned proximal of proximal end face 56. Likewise, each EDM wire 72 has a distal end 76 that is positioned distal of distal end face 58. Each EDM wire 72 is attached to a corresponding wire EDM that supplies each EDM wire 72 with a high frequency alternating current, but enables each EDM wire 72 to have five dimensions of free motion. In this position, proximal end 74 of each EDM wire 72 is moved independently in a circular orientation in a plane perpendicular to longitudinal axis L of stem body 54. Distal end 76 of each EDM wire 72 is, however, independently moved in a D-shaped orientation in a plane perpendicular to longitudinal axis L of stem body 54.

Figure 4B:
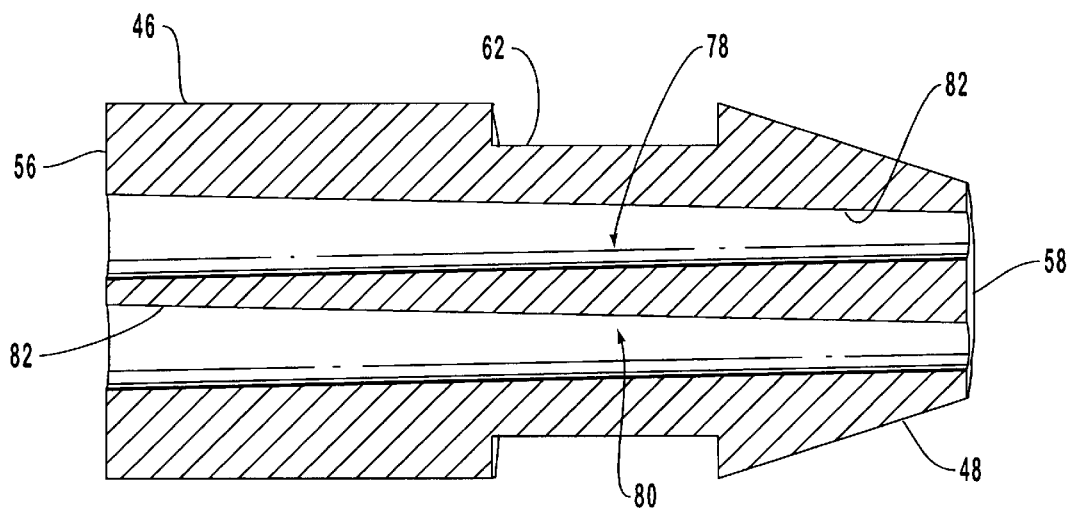

The movement of each EDM wire 72 electrostatically removes the portion of stem body 54 contacting each EDM wire 72. As depicted in FIG. 4B, the movement of each EDM wire 72 converts passageway 69 into a first fluid duct 78 and converts passageway 71 into a second fluid duct 80. Fluid ducts 78 and 80 are adjacently disposed and extend longitudinally between proximal end face 56 and distal end face 58 of stem body 54. Each of fluid ducts 78 and 80 has a smooth interior surface 82 that gradually and continuously transitions in cross-section from a circular shape at proximal end face 56 to a D-shape at distal end face 58. The smoothness of interior surface 82 helps prevent damage to any living cells in the fluid flowing therethrough.

Figure 4C:
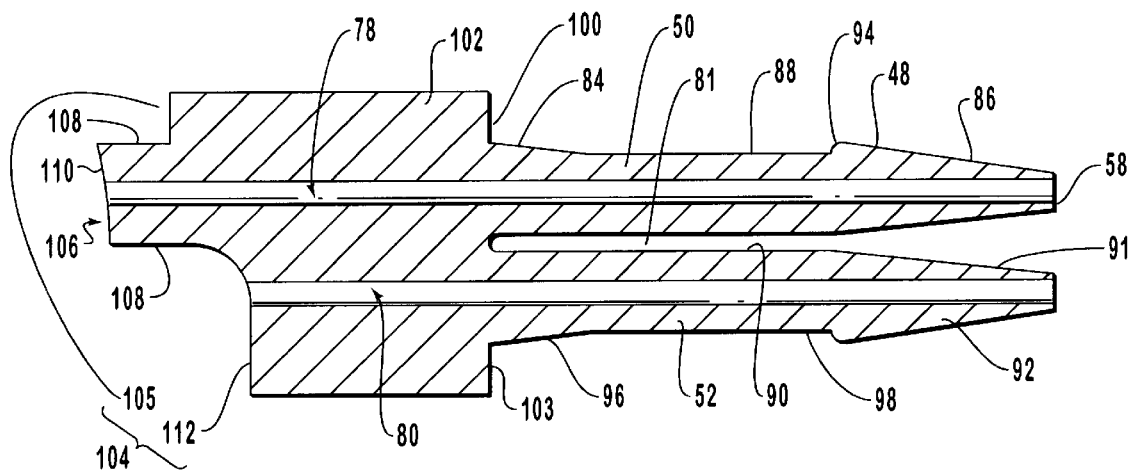
Figure 4D:
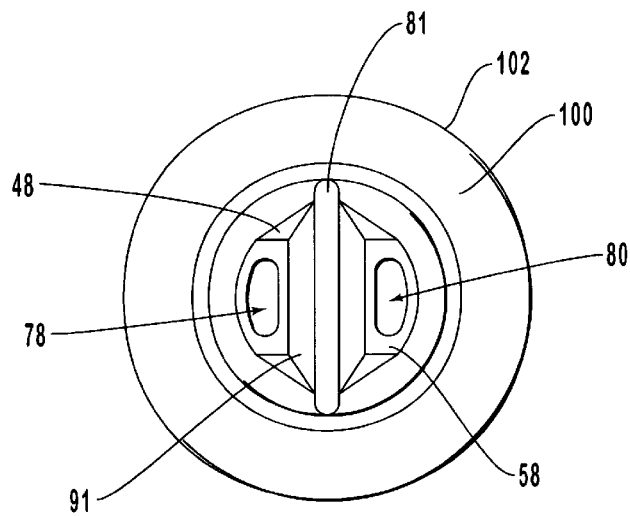
FIG. 4D is an elevated distal end view of the outlet stem shown in FIG. 4C.
Figure 4E:
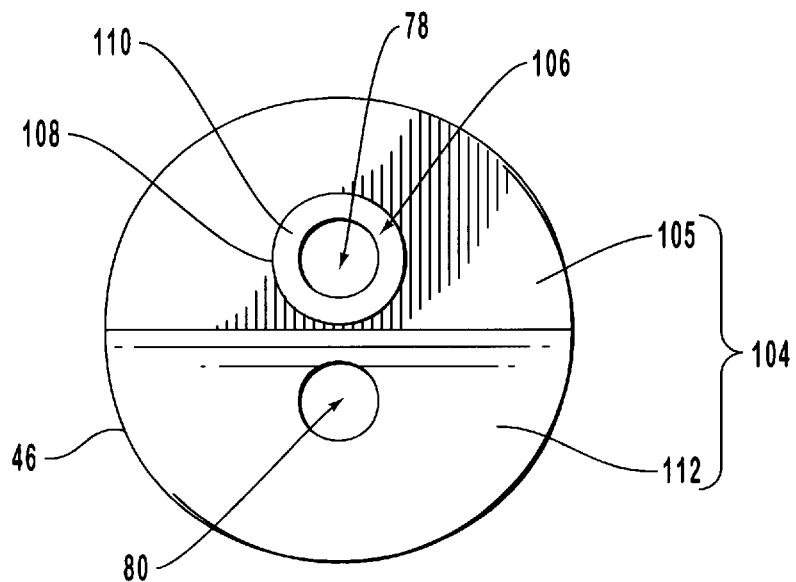
FIG. 4E is an elevated proximal end view of the outlet stem shown in FIG. 4C.

As best seen in FIG. 4D, fluid ducts 78 and 80 at distal end 48 of outlet stem 36 have a substantially D-shape transverse cross-section. In contrast, as depicted in FIG. 4E, fluid ducts 78 and 80 at proximal end 46 have a substantially circular transverse cross-section.

Although the cross-sectional shape of fluid ducts 78 and 80 changes along the length thereof, the transverse cross-sectional area of fluid ducts 78 and 80 are relatively constant at all points between proximal end face 56 and distal end face 58. This constant cross-sectional area, optimizes the flow rate achievable through fluid ducts 78 and 80.

By having the D-shaped cross-section the same area as the circular cross-section, it necessarily follows that the D-shaped cross-section has a minimum inside diameter that is smaller than the inside diameter of the circular cross-section. Accordingly, pilot holes 68 and 70 which are subsequently formed into the D-shaped cross-section are drilled having a smaller inner diameter than the inner diameter of pilot holes 64 and 66. Although pilot holes 64 and 66 could be formed having the same small inner diameter as pilot holes 68 and 70, pilot holes 64 and 66 having a larger inner diameter minimize the amount of material that is subsequently removed by EDM wire 72 in forming the circular cross-sectional areas.

As depicted in FIG. 4C, once fluid ducts 78 and 80 are completed, prongs 50 and 52 are created by cutting a slot 81 between fluid ducts 78 and 80 at distal end 48. Slot 81 may be formed using an EDM wire. Prongs 50 and 52 are shown as having a proximal end 84, a distal end 86, and a curved, exterior surface 88 that extends therebetween.

Exterior surface 88 is shown as comprising a locking barb 92 positioned at distal end 86 of each of prongs 50 and 52. Each locking barb 92 flares radially out from distal end face 58 to an outside ridge 94. Exterior surface 88 also includes a sloped transition shoulder 96 formed at proximal end 84. A cylindrical portion 98 extends between transition shoulder 96 and locking barb 92. Prongs 50 and 52 have an inner face 90 that is substantially flat. Opposing inner faces 90 define slot 81. A portion 91 of each inner face 90 flares radially outwardly at distal end 86 to facilitate the attachment to dual lumen catheter 20.

Outlet stem 36 is further shown in FIG. 4C as comprising a cylindrical barrel 102 having a distal end face 103 and an opposing proximal end face 104. Proximal ends 84 of prongs 50 and 52 are formed on distal end face 103 of barrel 102 so that prongs 50 and 52 project therefrom.

As shown in FIGS. 4C and 4E, proximal end face 104 of barrel 102 comprises a semicircular projecting end face 105 and an adjacent recessed end face 112. Recessed end face 112 is also semicircular and is formed distal of projecting end face 105. Second fluid duct 80 extends through recessed end face 112. Extending from projecting end face 105 is a cylindrical boss 106 having first fluid duct 78 extending therethrough. Boss 106 has a cylindrical sidewall 108 and an annular end face 110 that is slightly curved.

Figure 4F:
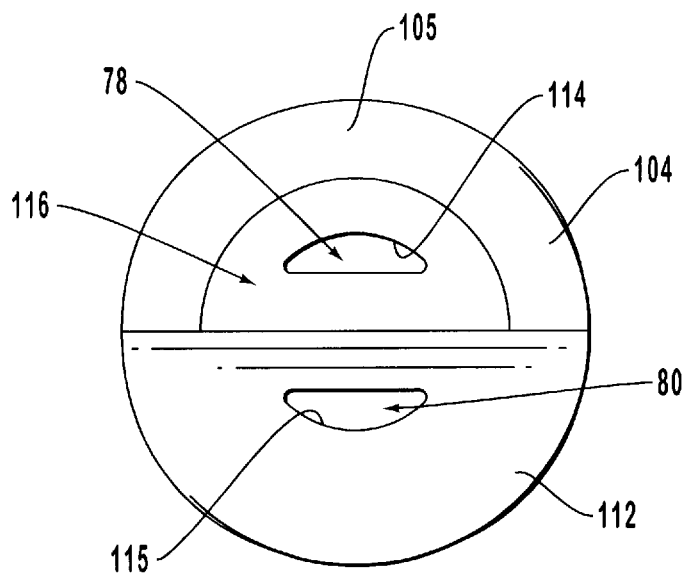
FIG. 4F is an elevated proximal end view of an alternative embodiment of the outlet stem shown in FIG. 4C.

In the illustrated embodiment proximal end 46 of fluid ducts 78 and 80 have a circular cross-section, as shown in FIG. 4E. In alternative embodiments, however, fluid ducts 78 and 80 can have any desired cross-sectional configuration. By way of example and not by limitation, as depicted in FIG. 4F proximal end 114 of fluid duct 78 and proximal end 115 of fluid duct 80 each have a D-shaped cross-section.

Although boss 106 in FIG. 4E has a circular transverse cross-section, boss 106 can also be formed in a variety of alternative configurations. By way of example and not by limitation, depicted in FIG. 4F is a boss 116 having a substantially D-shaped transverse cross-section.

Outlet stem 36 is made from a metal, such as stainless steel or titanium. Alternatively, it is conceivable that outlet stem 36 can be formed from other materials, such as plastics, ceramics, or composites.

Returning to FIG. 3, casing 28 comprises a top surface 118, a floor 120, and an annular sidewall 122 extending therebetween. Casing 28 has a figure-eight configuration that extends longitudinally between a proximal end 124 and an opposing distal end 126. Casing 28 could alternatively be circular or rectangular.

Formed in top surface 118 of casing 28 is a septum web recess 129. Septum web recess 129 is in part defined by a horizontally disposed seat 128 and a vertically oriented interior sidewall 130. Interior sidewall 130 encircles seat 128 and extends between seat 128 and top surface 118 of casing 28.

Figure 5:
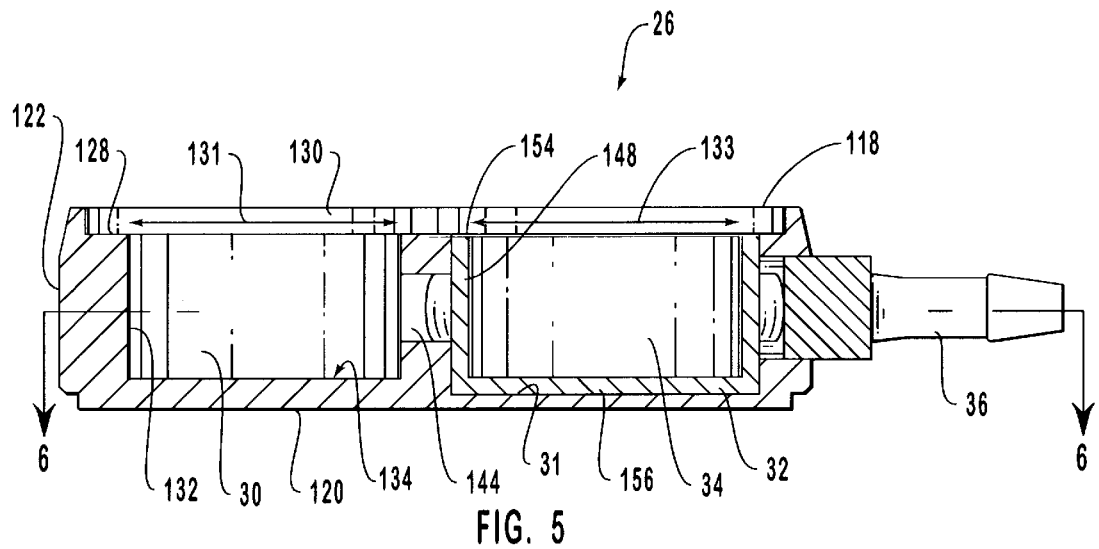
FIG. 5 is a cross-sectional side view of a subassembly of the access port shown in FIG. 2 taken along section line 5—5 shown in FIG. 3.

Counter bored within seat 128 at proximal end 124 of casing 28 is proximal fluid reservoir 30. As best shown in FIG. 5, seat 128 defines a space that includes a proximal access aperture 131 for proximal fluid reservoir 30 and a distal access aperture 133 for distal fluid reservoir 34. Proximal fluid reservoir 30 is further defined by a cylindrical sidewall 132 and a floor 134.

Referring to FIG. 3, counter bored within seat 128 at distal end 126 of casing 28 is distal cup 31 defined by a cylindrical sidewall 136 and a floor 138. Extending between proximal fluid reservoir 30 and distal cup 31 is a dividing wall 140.

A channel 142 is recessed within sidewall 136 of distal cup 31. Channel 142 extends from dividing wall 140 to a predetermined outlet location 141 at distal end 126 of casing 28. A transfer port 144 extends through dividing wall 140 to effect fluid communication between proximal fluid reservoir 30 and channel 142. An annular outlet port 146 extends through sidewall 122 of casing 28 at outlet location 141 to effect fluid communication between distal cup 31, channel 142, and the exterior of casing 28.

Open-topped basket 32 comprises an annular sleeve 148 having an interior surface 150 and an exterior surface 152. Sleeve 148 extends between a top edge 154 and a floor 156. Top edge 154 defines distal access aperture 133 that is encircled by sleeve 148. Extending between interior surface 150 and exterior surface 152 is an annular entry port 160. Alternatively, open-topped basket 32 can assume a smooth bowl-shaped interior rather than the cylindrical interior formed by sleeve 148 and floor 156.

Basket 32 and casing 28 are made from a metal such as stainless steel or titanium, but in the alternative could conceivably be formed from other materials, such as plastic, ceramics, or composites.

As depicted in FIG. 5, distal cup 31 is configured to receive open-topped basket 32 such that top edge 154 of basket 32 becomes flush with and forms part of seat 128. Top edge 154 is welded or otherwise secured to seat 128 in a fluid tight connection.

Figure 6:
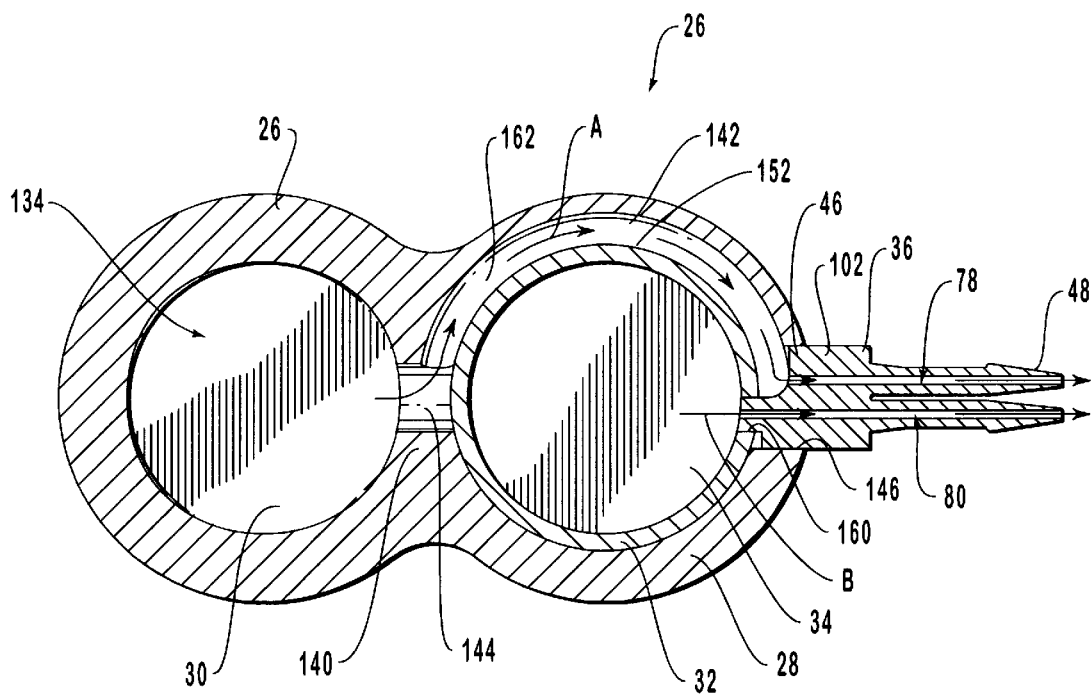
FIG. 6 is a cross-sectional top view of the subassembly of the access port shown in FIG. 5 taken along section line 6—6 shown therein.

Basket 32 is disposed within distal cup 31 with entry port 160 of basket 32 in alignment with outlet port 146 of casing 28. As best depicted in FIG. 6, barrel 102 of outlet stem 36 is as a result received within outlet port 146, while boss 106 is simultaneously received within entry port 160 of basket 32. Conventional titanium welding techniques or other securing processes are used to provide a fluid seal between barrel 102 of stem 36 and casing 28. Similar techniques are used to provide a fluid seal between boss 106 of outlet stem 36 and basket 32.

Boss 106 and barrel 102 each of outlet stem 36 can be formed in a variety of alternative configurations as long as entry port 160 of basket 32 is configured to complementarily receive boss 106. Outlet port 146 of casing 28 must similarly be configured to complementarily receive barrel 102. It has been found to be easiest to align and secure boss 106 into entry port 160 and barrel 102 into outlet port 146, if entry port 160 of basket 32 and boss 106 of outlet stem 36 have complementary circular configurations, and outlet port 146 of casing 28 and barrel 102 of outlet stem 36 have complementary circular configurations.

With casing 28, basket 32, and outlet stem 36 interconnected as discussed above, discrete fluid communication is provided between proximal fluid reservoir 30 and outlet stem 36 and also between distal fluid reservoir 34 and outlet stem 36. As depicted by arrows A in FIG. 6, fluid in proximal fluid reservoir 30 flows through transfer port 144 in dividing wall 140 and enters a fluid flow pathway 162 to travel around the perimeter of basket 32. Fluid flow pathway 162 is completely formed only upon the insertion of basket 32 into distal cup 31. Fluid flow pathway 162 is thus bounded by channel 142 of casing 28 and exterior surface 152 of basket 32. From fluid flow pathway 162, the fluid enters proximal end 46 of first fluid duct 78 and is subsequently discharged from distal end 48 of first fluid duct 78.

As depicted by arrow B in FIG. 6, fluid in distal fluid reservoir 34 flows directly into proximal end 46 of second fluid duct 80 and therethrough for discharge at distal end 48 thereof.

Figure 6A:
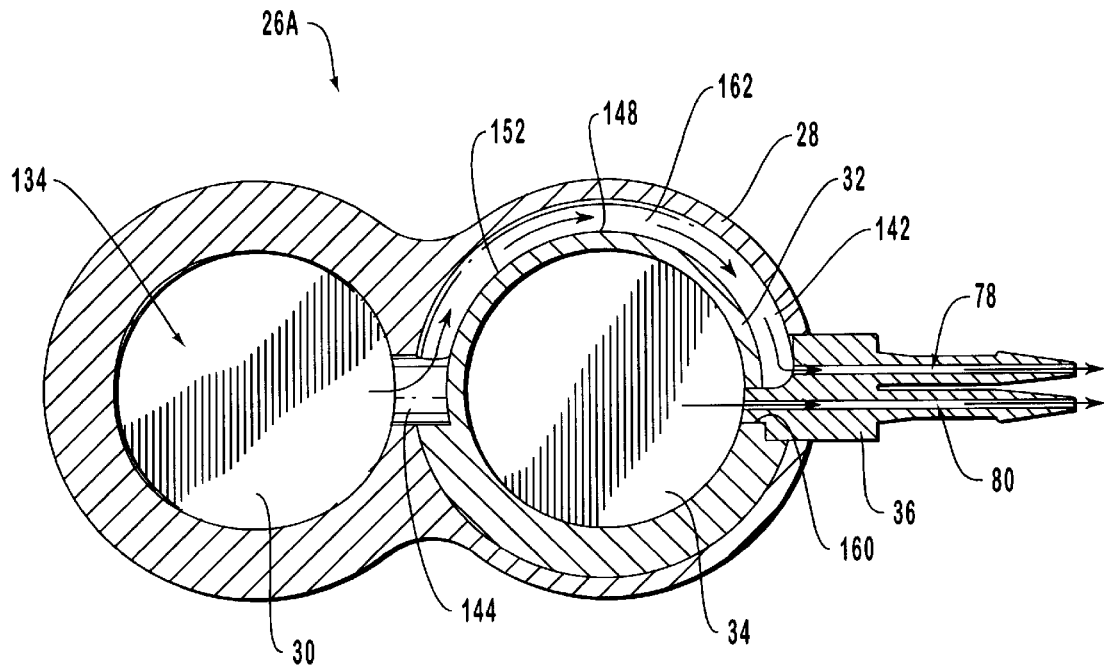
FIG. 6A is a cross-sectional top view of an alternative embodiment of the subassembly of the access port shown in FIG. 6 wherein the fluid flow pathway extending from the proximal reservoir to the stem is formed in the sidewall of the basket.

FIG. 6A illustrates an alternative embodiment of a housing 26A. As shown in FIG. 6A, fluid flow pathway 162 is still bounded between casing 28 and a basket 32A, but channel 142 is recessed in the exterior surface 152A of basket 32A, rather than being recessed in annular sidewall 136 of distal cup, as was the case with housing 26 illustrated in FIGS. 5 and 6.

Figure 6B:
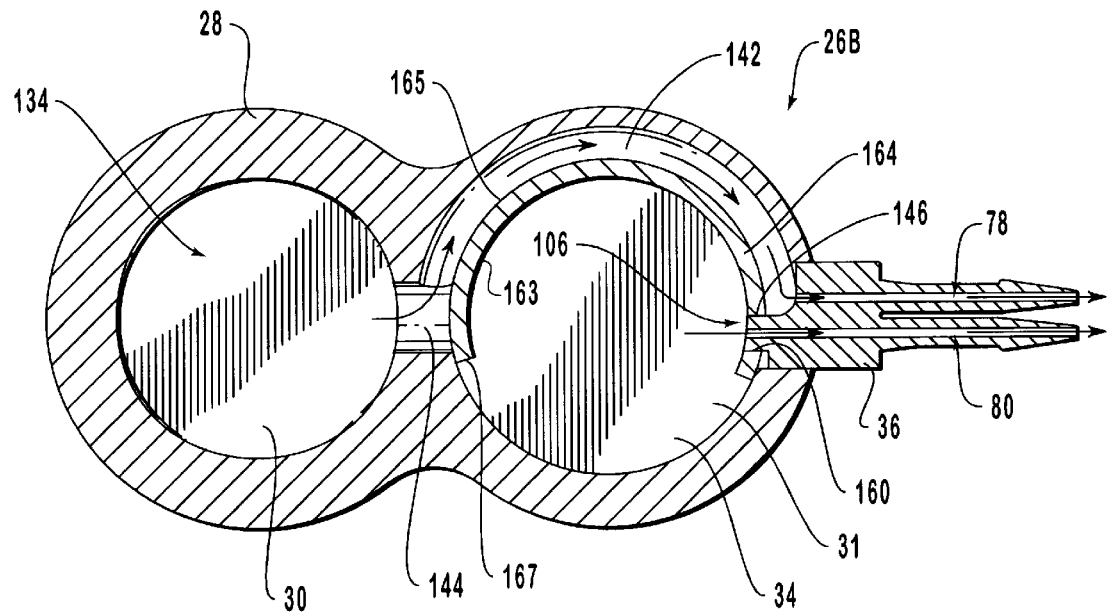
FIG. 6B is a cross-sectional top view of an alternative embodiment of the subassembly shown in FIG. 6 wherein the basket has been replaced by a C-shaped sleeve.

In another alternative embodiment of a housing 26B shown in FIG. 6B, basket 32 of FIGS. 3,5 and 6 has been replaced by a C-shaped sleeve 164 having an interior surface 163, an exterior surface 165, and an outside edge 167. An entry port 160 extends between interior surface 163 and exterior surface 165. C-shaped sleeve 164 is large enough to cover transfer port 144, channel 142, and outlet port 146. Thus, discrete fluid communication is enabled from proximal fluid reservoir 30 to first fluid duct 78 and between a distal fluid reservoir 34B and second fluid duct 80.

In housing 26B, distal fluid reservoir 34B is defined by the volume bounded by interior surface 163 of C-shaped sleeve 164 and the portion of distal cup 31 not covered by C-shaped sleeve 164. To prevent fluid communication between proximal fluid reservoir 30 and distal fluid reservoir 34B, it may also be necessary to weld or otherwise seal all points of outside edge 167 of C-shaped sleeve 164 to distal cup 31.

Figure 6C:
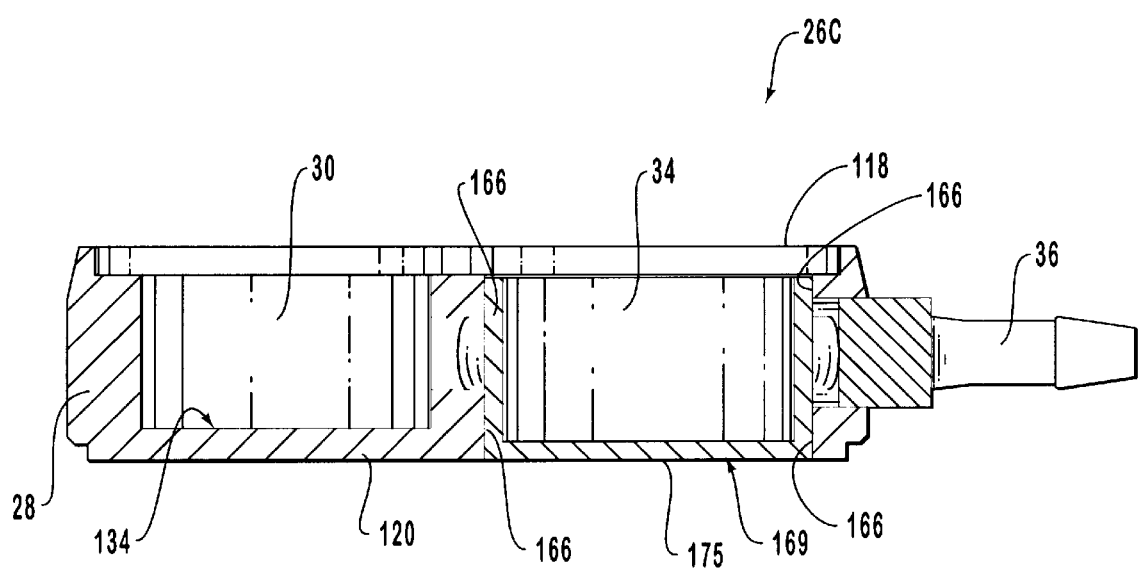
FIG. 6C is a cross-sectional side view of an alternative embodiment of the subassembly of the access port shown in FIG. 6 wherein the basket extends through the casing.

Another alternative embodiment of a housing 26C is depicted in FIG. 6C. As shown therein, casing 28 is configured such that an open-topped basket 169 having a floor 175 and enclosing a distal fluid reservoir 34C is received in a passageway 166 formed without interruption through casing 28 from top surface 118 to and through floor 120. Floor 175 of basket 169 is then flush with floor 120 of casing 28 and visible from the exterior of casing 28. Basket 169 otherwise has the same elements as basket 32 of the earlier embodiments and interacts with casing 28 in substantially the same way as previously discussed with regard to basket 32.

Figure 13:
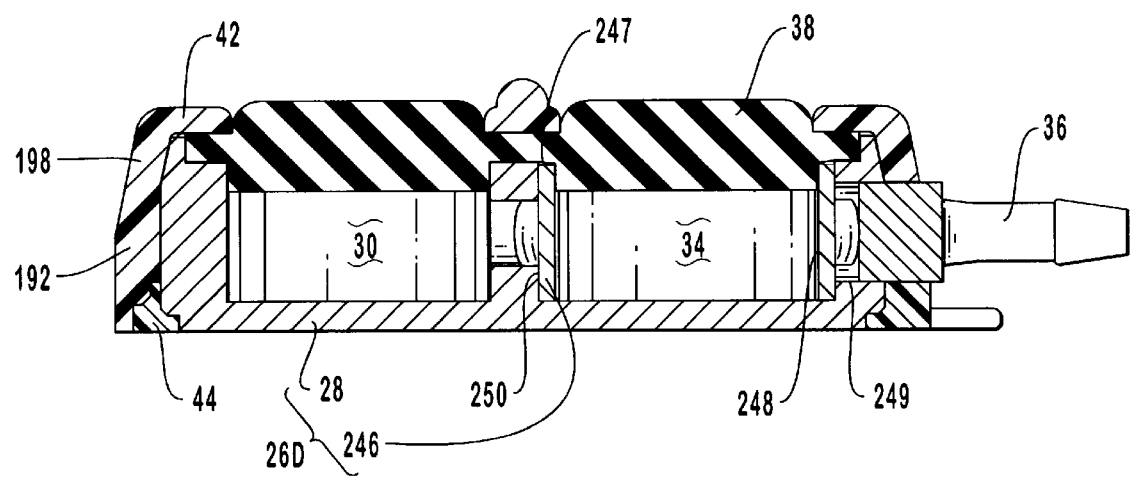
FIG. 13 is a cross-sectional side view of an alternative embodiment of the access port shown in FIG. 3 wherein the basket has been replaced by an annular sleeve not having a floor.

FIG. 13 also shows a final alternative embodiment of a housing 26D. As disclosed therein, basket 32 has been replaced by an annular sleeve 246 having a top edge 247 and a bottom edge 249. Sleeve 246 also has an interior surface 248, an exterior surface 250, and an entry port extending therebetween that is substantially similar to entry port 160 shown in FIGS. 6, 6A, and 6B.

Sleeve 246 is used in the same way as discussed above with regard to basket of FIGS. 3, 5 and 6. The distinction between basket 32 and annular sleeve 246 is that annular sleeve 246 does not include any floor, such as floor 156 basket 32. In housing 26D, a distal fluid reservoir 34D is defined by the volume bounded by interior surface 248 of annular sleeve 246 and the portion of distal cup 31 not covered thereby. As a result, bottom edge 249 of annular sleeve 246 should be welded or otherwise sealed to distal cup 31 to prevent fluid communication between proximal fluid reservoir 30 and distal fluid reservoir 34.

In one embodiment of the present invention, fluid coupling means are provided for effecting a sealed fluid communication between second fluid duct 80 and distal fluid reservoir 34. By way of example and not by limitation, one embodiment of the fluid coupling means includes boss 106 of outlet stem 36, that is connected with distal fluid reservoir 34 through outlet port 146 of casing 28 in combination with entry port 160 of basket 32.

Alternative embodiments of such a fluid coupling means could include the alternative configurations of boss 106 previously discussed with regard to FIG. 4F, and the alternative structures through which entry port 160 is formed in the embodiments of housings previously discussed with regard to FIGS. 6A–6C and FIG. 13. A discrete passageway could be formed through casing 28 and basket 32 in use for communicating with second fluid duct 80. Alternatively, boss 106 could project from basket 32 and pass through casing 28 to connect with second fluid duct 80 in outlet stem 36.

The present invention also provides fluid conduit means between casing 28 and a sleeve for placing proximal fluid reservoir 30 in fluid communication with first fluid duct 78 in outlet stem 36. By way of example and not by limitation, one example of such a fluid conduit means includes fluid flow pathway 162 formed by channel 142 recessed within sidewall 136 of distal cup 31 and basket 32 received within distal cup 31, as previously discussed with regard to FIGS. 3, 5, and 6. Transfer port 144 allows fluid to flow from proximal fluid reservoir 30 to fluid flow pathway 162. Outlet port 146 allows fluid to flow between fluid flow pathway 162 and outlet stem 36.

Alternative embodiments of such a fluid conduit means include a channel 142 recessed in an exterior surface of basket 32, as in FIG. 6A or the various structures shown in FIGS. 6B, 6C, and 13 as being received in distal cup 31 so as to close channel 142.

The present invention also includes delivery means for effecting discrete fluid communication between each of fluid reservoirs 30 and 34 and the exterior of housing 26. By way of example and not by limitation, such a delivery means includes each of the disclosed structures and alternative embodiments of a fluid coupling means and also each of the disclosed structures and alternative embodiments of a fluid conduit means.

Figure 7:
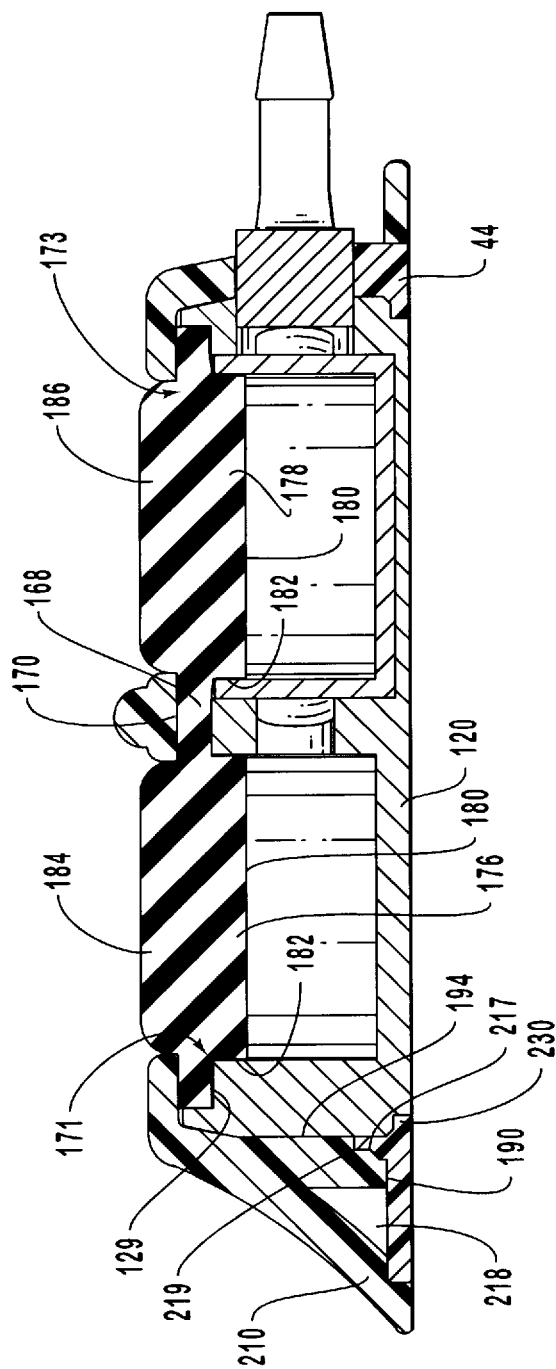
FIG. 7 is a cross-sectional side view of the subassembly of the access port shown in FIG. 2 taken along section line 7—7 shown therein.
Figure 8:
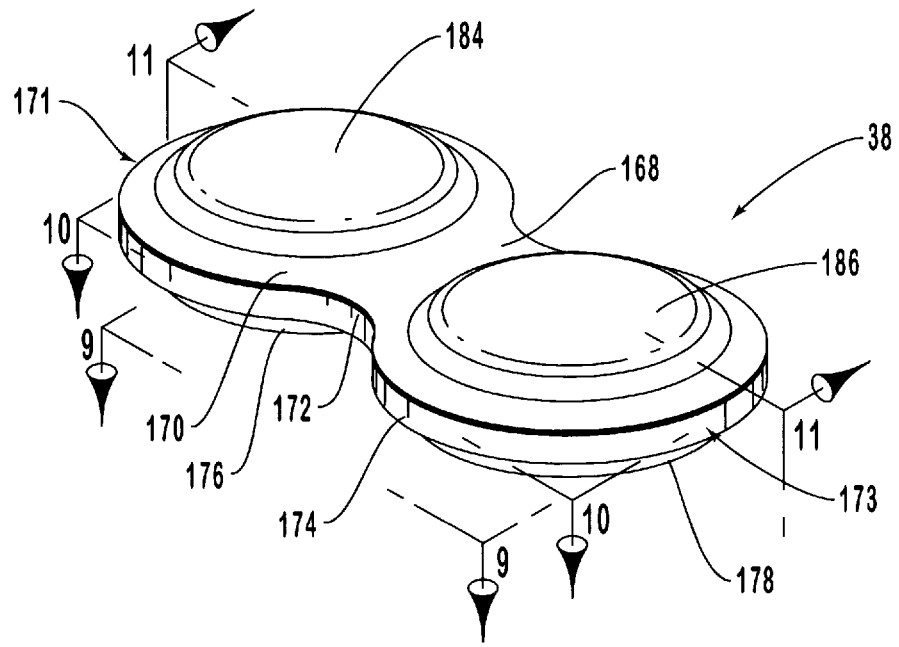
FIG. 8 is a perspective view of the compound septum in a compressed state as shown in FIG. 7.

Referring again to FIGS. 3 and 5, compound septum 38 is used for covering and sealing proximal access aperture 131 and distal access aperture 133. As shown in FIGS. 7 and 8, compound septum 38 includes a planar septum web 168 having a top surface 170, a bottom surface 172, and a side surface 174 extending therebetween. Compound septum 38 also extends longitudinally between a proximal end 171 and a distal end 173. As will be discussed later in greater detail, connecting web 168 is configured to be snugly received within septum web recess 129 of casing 28.

Projecting from bottom surface 172 of connecting web 168 is a cylindrical proximal plug 176 and a cylindrical distal plug 178. As best seen in FIG. 7, each of proximal plug 176 and distal plug 178 has a bottom face 180 with an annular sidewall 182 extending between bottom surface 172 of connecting web 168 and bottom face 180.

Referring to FIG. 8, compound septum 38 also comprises a proximal needle target dome 184 and a distal needle target dome 186 each projecting from top surface 170 of connecting web 168. Proximal needle target dome 184 is aligned with proximal plug 176. Likewise, distal needle target dome 186 is aligned with distal plug 178.

Compound septum 38 is preferably made of a compressible and resiliently deformable material that, for example, enables a needle to pass through proximal needle target dome 184, connecting web 168, and proximal plug 176 into proximal fluid reservoir 30. In one embodiment, compound septum 38 is made from a medical grade silicone. In alternative embodiments, compound septum 38 can also be made from other medical grade elastomers or rubbers.

Returning again to FIG. 3, clamp 40 is used to secure compound septum 38 to housing 26. Clamp 40 includes a cap 42 and a shoe 44. Cap 42 is shown as having a top surface 188, a bottom surface 190, and a sidewall 192 that extends therebetween. Cap 42 also has a proximal end 198 and an opposing distal end 200.

Extending through top surface 188 of cap 42 at proximal end 198 is a proximal aperture 202. Likewise, extending through top surface 188 at distal end 200 is a distal aperture 204. Apertures 202 and 204 are configured to receive needle target domes 184 and 186 of compound septum 38, respectively.

Located on top surface 188 and extending between proximal aperture 202 and distal aperture 204 is a bridge 206. Upstanding on bridge 206 is a tactile locating ridge 208 the position of which can be ascertained by a medical practitioner through palpating the skin of patient 10 at the implantation site for access port 18. Once the position of tactile locating ridge 208 is thusly ascertained, the position of proximal fluid reservoir 30 and of distal fluid reservoir 34 on either side thereof is also automatically determined. Tactile locating ridge 208 thus facilitates accurate targeting of the needle of syringe 23 into either proximal fluid reservoir 30 or distal fluid reservoir 34.

Projecting proximally outward at proximal end 198 of cap 42 is a sloped nose 210. Sloped nose 210 enables easy insertion of access port 18 into a subcutaneous implantation pocket in the skin of patient 10. Extending through sidewall 192 of cap 42 at distal end 200 is a stem slot 212. Stem slot 212 is configured to receive outlet stem 36 when housing 26 is disposed in clamp 40.

Radially projecting out from sidewall 192 of cap 42 at opposing sides of stem slot 212 are tabs 214 that each have a suture slot 216 formed therethrough. Suture slots 216 are used to suturing access port 18 in an implantation pocket in the skin of patient 10.

Cap 42 includes an interior surface 194 that defines a receiving chamber 196. As better seen in FIG. 7, an annular attachment groove 217 is formed on interior surface 194 at bottom surface 190.

Interior surface 194 defines a cavity 218 at proximal end 198 of cap 42. Cavity 218 is formed to minimize material costs and also to form cap 42 having a relatively constant thickness at all points about cap 42. Cap 42 is preferably molded from a medical grade plastic. In alternative embodiments, cap 42 can also be made from metals, ceramics, or composites. By forming cap 42 with a relatively constant material thickness, deformation resulting from different rates of cooling of the molded plastic or other materials is minimized.

Shoe 44 is shown in FIG. 3 as comprising an attachment ridge 219 having a top edge 220 and a bottom edge 222. Attachment ridge 219 also includes an exterior surface 226 and an interior surface 228. Radially extending inward from interior surface 228 at bottom edge 222 is a lip 230. Shoe 44 also has a proximal end 232 and an opposing distal end 234. Projecting from exterior surface 226 at proximal end 232 is a tongue 236. Positioned at distal end 234 is a grooved stem carriage 238.

One of the novel features of the present invention is the configuration of compound septum 38 and the use thereof to cover and seal proximal access aperture 131 and distal access aperture 133.

A single compound septum 38 is used to cover and seal both of reservoirs 30 and 34. Compound septum 38 not only prevents the passage of fluid between proximal fluid reservoir 30 and distal fluid reservoir 34, but also prevents the transfer of fluids between the exterior of access port 18 and either of reservoirs 30 or 34. By using a single compound septum 38 rather than two individual septums, reservoirs 30 and 34 can be positioned closer together in housing 26, thereby decreasing the overall size of access port 18.

Compound septum 38 is configured to have desired properties when compound septum 38 is incorporated into access port 18. For example, when a needle is passed through compound septum 38 into one of reservoirs 30 or 34, septum 38 effectively seals around the exterior of the needle to prevent the passage of fluids between septum 38 and the exterior of the needle. Septum 38 is also configured to exhibit a predetermined amount of needle retention force, once septum 38 is installed in access port 18. Needle retention force refers to the tendency of septum 38 to resist removal of a penetrating needle.

The sealing effectiveness and needle retention of septum 38 is in part related to the amount of radial compressive force applied to septum 38 by housing 26 and clamp 40. In general, the greater the compressive force applied to septum 38, the higher the sealing effectiveness and needle retention.

The compressive force on septum 38, however, must not be so great that inserting the needle through compound septum 38 results in the needle coring septum 38. Coring occurs where the stress on the installed septum 38 is so high that when the needle is inserted into septum 38, a portion of septum 38 is forced inside the needle. The portion of septum 38 forced inside the needle is then severed from septum 38, resulting in a small passage extending through septum 38. Continued coring eventually results in septum failure.

Access port 18 is generally subcutaneously placed making it difficult to direct exactly where the needle will pass through septum 38. Compound septum 38 is thus configured to have substantially uniform properties across the exposed area thereof when installed in access port 18. That is, the interaction between septum 38 and a needle should be substantially similar independent of where the needle is passed through septum 38.

To achieve the foregoing objectives with regard to compound septum 38, proximal plug 176 has an outside perimeter defined by sidewall 182. Furthermore, proximal fluid reservoir 30 has an inside perimeter defined by interior sidewall 130. The outside perimeter of proximal plug 176 is slightly larger than the inside perimeter of proximal fluid reservoir 30. The difference in perimeter sizes is sufficiently small to allow proximal plug 176 to be manually received within proximal fluid reservoir 30 without causing buckling of proximal plug 176. As a result of the size differential, radially inwardly uniform force is applied around the perimeter of proximal plug 176 when proximal plug 176 is received within proximal fluid reservoir 30. This radially inward force applied to proximal plug 176 is designated by arrows $R_1$ shown in FIG. 9.

Figure 9:
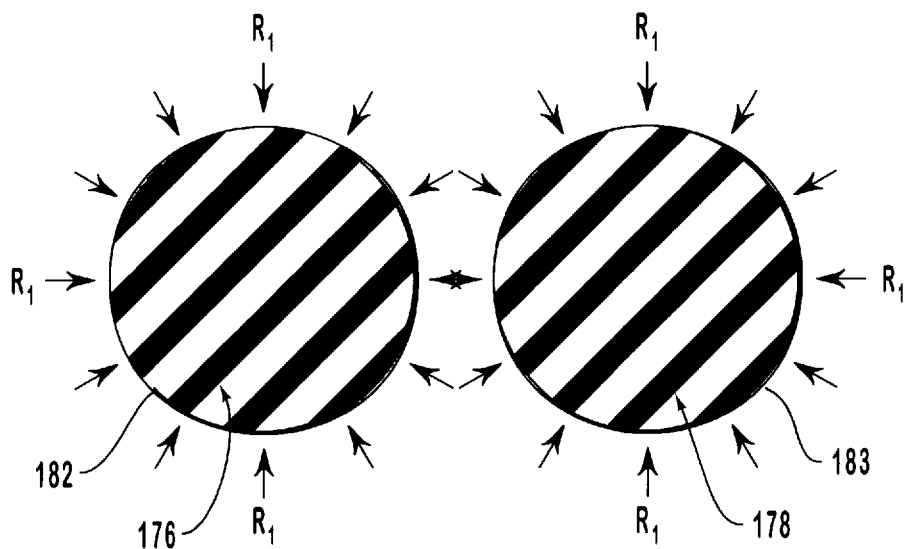
FIG. 9 is a cross-sectional top view of plugs projecting from the compound septum shown in FIG. 8 and taken along section line 9—9 shown therein.

Distal plug 178 has the same size relationship to distal fluid reservoir 34 as proximal plug 176 has to proximal fluid reservoir 30. Accordingly, as also depicted in FIG. 9, radially uniform force $R_1$ is applied to sidewall 183 around the perimeter of distal plug 178 when distal plug 178 is disposed within distal fluid reservoir 34.

Septum web 168 also has an outside perimeter defined by side surface 174. Furthermore, septum web recess 129 has an inside perimeter defined by interior sidewall 130. The exterior perimeter of septum web 168 is larger than the interior perimeter of septum web recess 129. The difference in perimeter sizes is sufficiently small to allow septum web 168 to be manually received within septum web recess 129 without causing significant buckling in compound septum 38. As a result, interior sidewall 130 of septum web recess 129 radially inwardly compresses side surface 174 of septum web 168, when connecting web 168 is received within septum web recess 129. This relatively uniform, radially inwardly directed force on septum web 168 is designated by arrows $R_2$ shown in FIG. 10.

Figure 10:
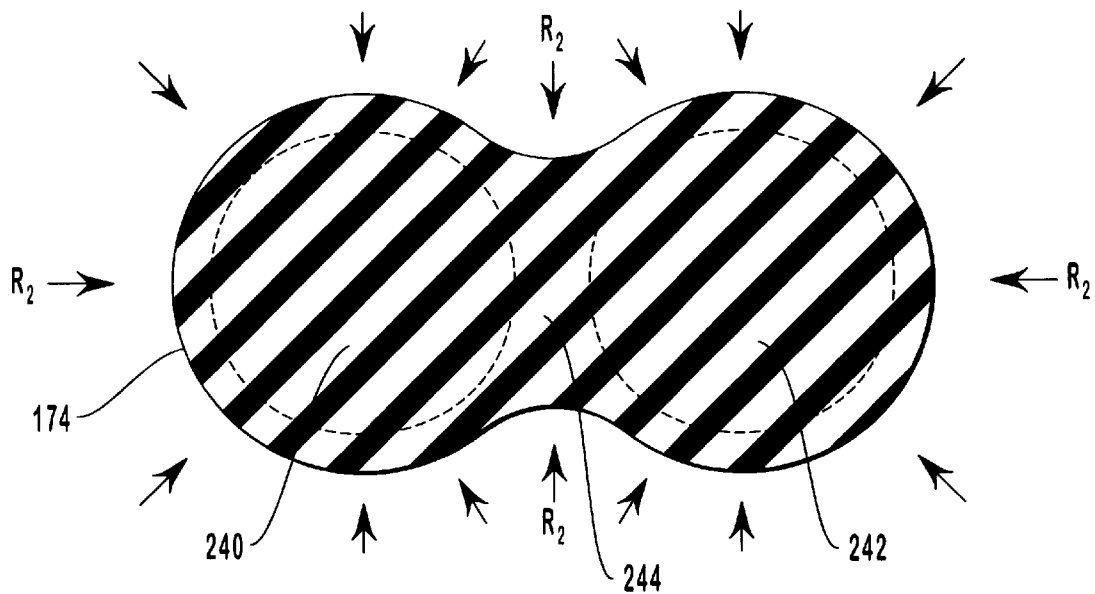
FIG. 10 is a cross-sectional top view of the connecting web of the compound septum shown in FIG. 8 and taken along section line 10—10 as shown therein.

As also shown in FIG. 10, septum web 168 includes a proximal sealing portion 240, which is defined as the area of septum web 168 above proximal plug 176. Septum web 168 also includes a distal sealing portion 242, which is defined as the area of septum web 168 positioned above distal plug 178. Furthermore, septum web 168 also includes a central portion 244 between proximal sealing portion 240 and distal sealing portion 242.

As seen in FIG. 10, the radial force $R_2$ imposed by interior sidewall 130 of housing 26 is not uniform around proximal sealing portion 240 and distal sealing portion 242. More specifically, no radial force is applied at central portion 244 of septum web 168 that radially biases against sealing portions 240 and 242. As such, the stresses applied across sealing portions 240 and 242 by interior sidewall 130 of septum web recess 129 are not uniform.

To remedy this lack of uniformity in forces applied to septum web 168, the height of side surface 174 of septum web 168 is slightly greater than the height of interior sidewall 130 of septum web recess 129. As a result, when compound septum 38 is received within septum web recess 129, side surface 174 projects above top surface 118 of interior sidewall 130.

To assemble the components of access port 18, housing 26 and compound septum 38 are received within receiving chamber 196 of cap 42. Compound septum 38 is positioned with proximal needle target dome 184 is within proximal aperture 202 of cap 42 and distal needle target dome 186 within distal aperture 204 of cap 42. Shoe 44 is then aligned with bottom surface 190 of cap 42. As shown in FIG. 7, shoe 44 is pressed against cap 42 to seat floor 120 of casing 28 on lip 230 of shoe 44 and to position attachment ridge 219 of shoe 44 within attachment groove 217 of cap 42.

Figure 11:
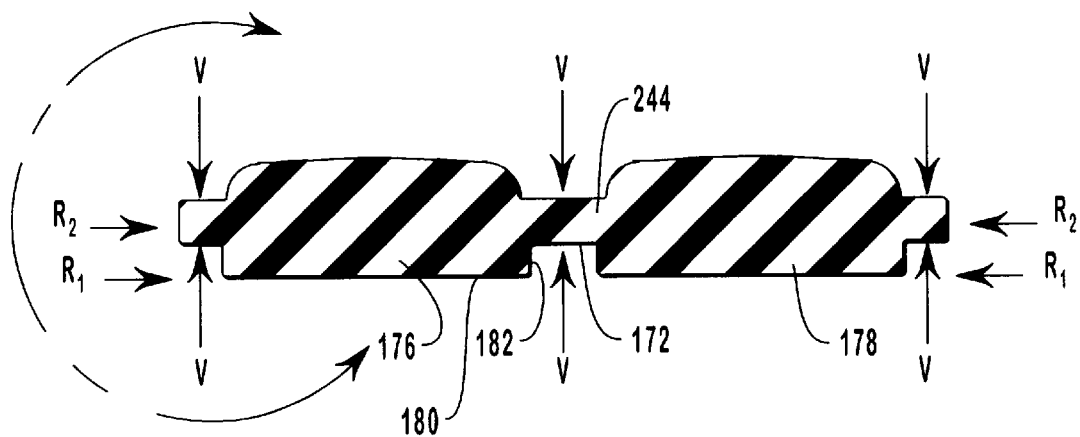
FIG. 11 is a cross-sectional side view of the compound septum shown in FIG. 8 taken along section line 11—11 as shown therein.

As a result, compound septum 38 is compressed between housing 26 and cap 42. Septum web 168 is compressed between seat 128 of housing 26 and interior surface 194 of cap 42. This results in an axial compressive force V being applied to septum web 168 as illustrated in FIG. 11.

Figure 12:
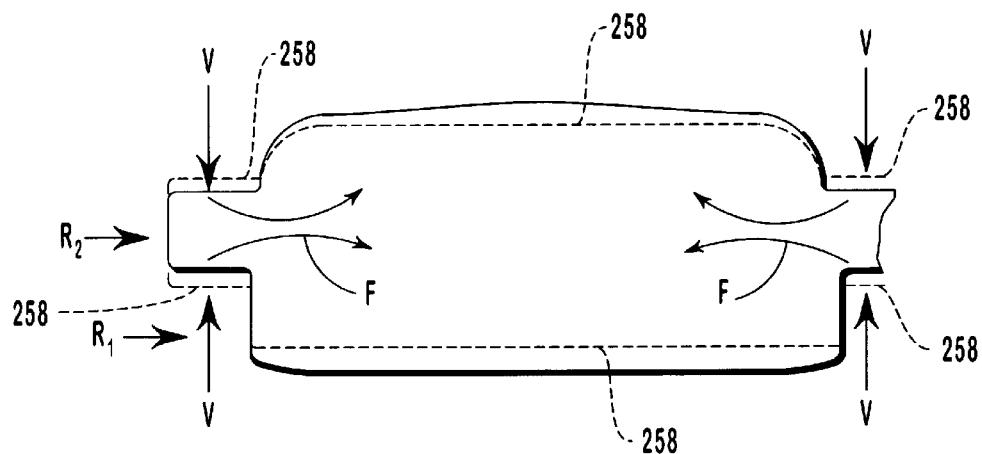
FIG. 12 is a schematic representation of the flow of the compound septum as it is compressed into the state shown in FIG. 7.

In FIG. 12 dash lines 258 depict compound septum 38 prior to the application of the vertical compressive force V, while the solid lines show the resulting shape of compound septum 38 after the application of compressive force V. As a result of the flexible nature of the material from which compound septum 38 is formed, the application of compressive force V results in a portion of the compressed material radially flowing inward towards proximal sealing portion 240 and distal sealing portion 242. The flow of material is represented by the arrows F. The portion of septum web 168 subject to the compressive force V decreases in thickness while the flow of material causes the remaining portion of septum 38 to increase in thickness.

Compressive force V is uniformly applied around the perimeter of each of sealing portions 240 and 242. As a result of the lateral flow F of material, compressive force V is converted into a horizontal compressive force that is uniformly distributed around the area of sealing portions 240 and 242 of septum web 168.

The combination of these forces being applied to compound septum 38 results not only in compound septum 38 sealing access apertures 131 and 158, but in relatively uniform compressive forces about the sealing portions 240 and 242 of septum web 168 that produce desired needle sealing and retention properties in the installed septum.

With compound septum 38 therebetween, cap 42 and shoe 44 are ultrasonically welded or otherwise secured together at bottom surface 190 of cap 42. The securing of cap 42 to shoe 44 maintains compound septum 38 biased against housing 26 and imparts the above-described properties in compound septum 38. Cap 42 may only be spot welded to shoe 44 leaving an open seam therebetween that is large enough to admit a sterilizing gas, such as ethylene oxide, but small enough to preclude passage of blood therethrough.

In one embodiment of the present invention, clamping means are provided for securing septum 38 against housing 26 in sealing engagement with each of the access apertures therein. By way of example and not limitation, one embodiment of such a clamping means includes cap 42 and shoe 44 as previously discussed with regard to FIGS. 3 and 7. An alternative embodiment of the clamping means is depicted in FIG. 13, where nose 210 is absent from cap 42 and shoe 44 includes no tongue 236. Sidewall 192 of cap 44 is substantially flat at proximal end 198. In yet other embodiments, the ridge and groove configuration for connecting cap 42 and shoe 44 can be reversed. Conventional connecting structures could be used to enable cap 42 and shoe 44 to be snapped together.

Figure 14:
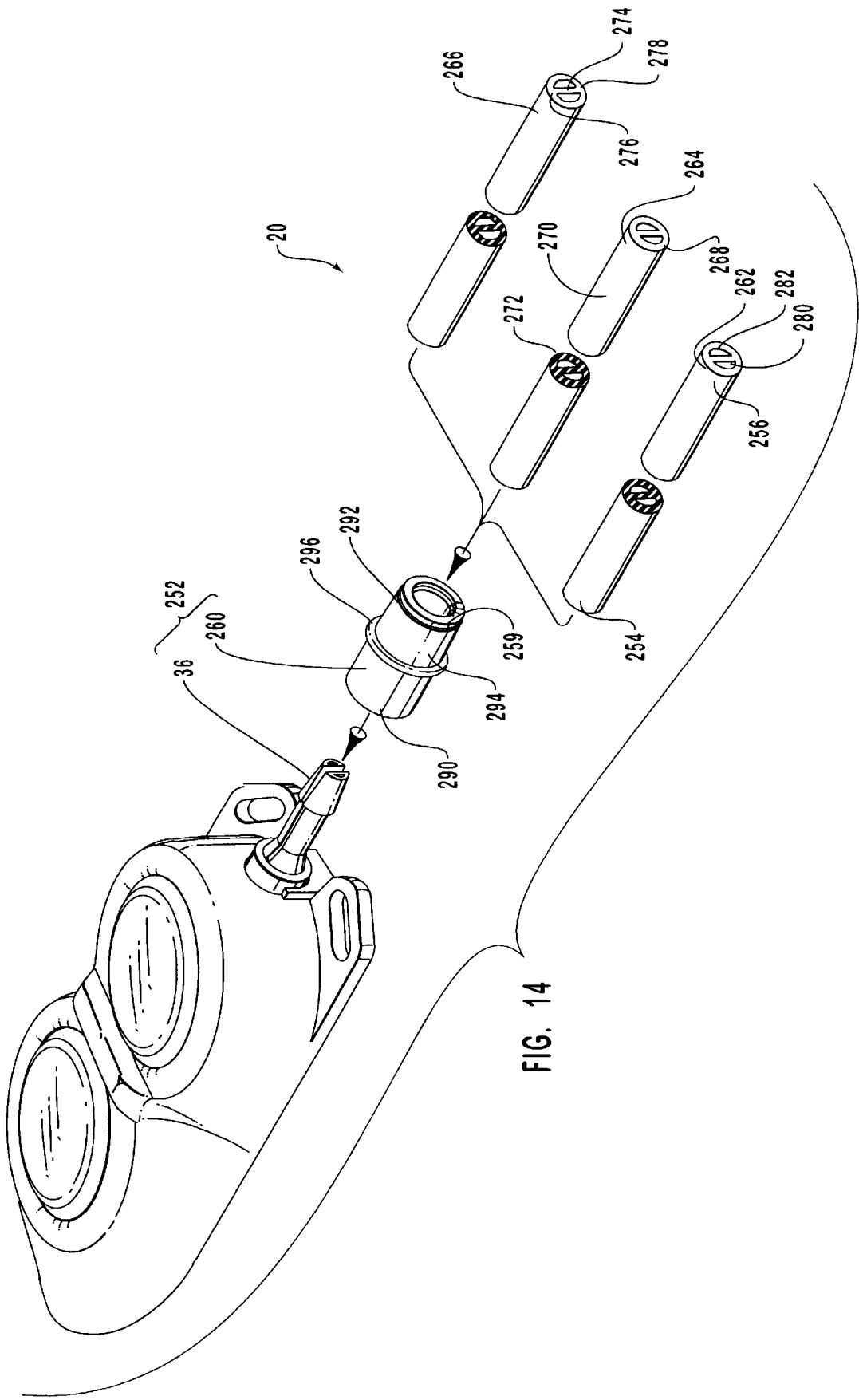
FIG. 14 is a perspective view of a multiple-catheter connection system where one of three unique dual lumen catheters is selectively attached to the access port shown in FIG. 3 by a locking sleeve.

As depicted in FIG. 14, the present invention also includes a catheter connection system 252 for effecting a fluid tight coupling and a mechanical joiner between a medical device, such as access port 18, and a select dual lumen catheter 20 chosen from among a plurality of three dual lumen catheters. Catheter connection system 252 includes outlet stem 36, as described above, and locking sleeve 260.

Locking sleeve 260 is shown as having a proximal end 290, an opposing distal end 292, and an exterior surface 294 extending therebetween. Encircling and extending radially outwardly from exterior surface 294 is an annular bias ring 296. Bias ring 296 is used for gripping and advancing locking sleeve 260.

The present invention also includes gripping means for increasing frictional engagement with exterior surface 294 of locking sleeve 260. By way of example and not by limitation, one embodiment of the gripping means includes bias ring 296. In alternative embodiments of the gripping means can include bias rings having a variety of cross-sectional configurations. The gripping means could also comprise an exterior surface, such a exterior surface 294, comprised of two different outside diameters with a shoulder extending for use to selectively bias locking sleeve 260.

Encircling exterior surface 294 at distal end 292 of locking sleeve 260 is an annular dye notch 259, which is configured to receive a dye, such as an ink, that readily visually distinguishes distal end 292 from proximal end 290. In this way, it is easy for the user of locking sleeve 260 to ascertain in which orientation locking sleeve 260 is to be used. The ink used for this purpose can advantageously be radiopaque by including, for example, a quantity of tungsten therein.

Figure 15:
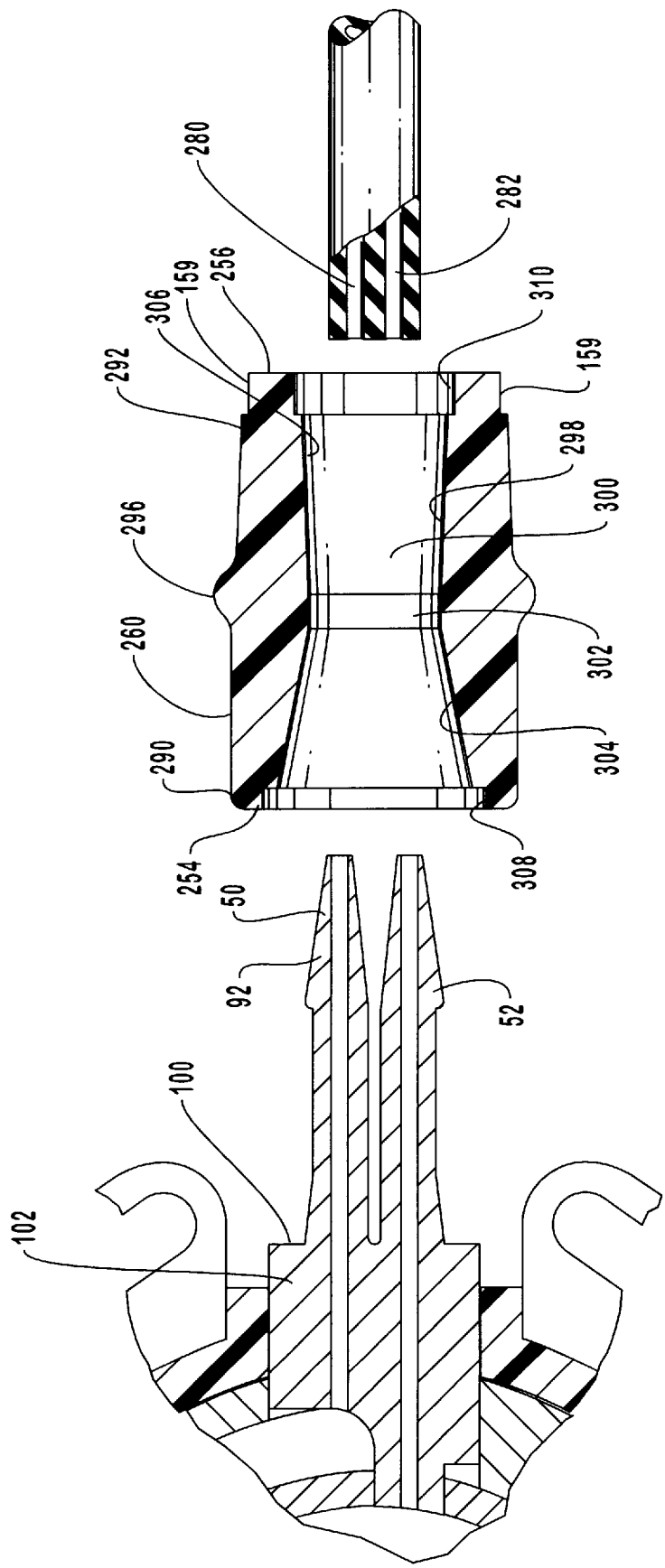
FIG. 15 is a cross-sectional top view of a selected catheter in preparation for attachment to the stem of the access port as shown in FIG. 14.

As shown in FIG. 15, locking sleeve 260 also includes an interior surface 298 that defines a passageway 300 longitudinally extending between a proximal end face 254 and a distal end face 256. Interior surface 298 is shown as comprising an annular locking ring 302, a first frustoconical portion 304 that radially slopes outward from locking ring 302 toward proximal end 290, and a second frustoconical portion 306 that radially slopes outward from locking ring 302 toward distal end 292 of locking sleeve 260. Recessed in proximal end face 254 is an enlarged cylindrical recess 308 that extends to first frustoconical portion 304. A cylindrical recess 310 is also formed at distal end face 256 and extends to second frustoconical portion 306.

Referring to FIG. 14, selected catheter 20 is chosen from a first dual lumen catheter 262, a second dual lumen catheter 264, and a third dual lumen catheter 266. Each of dual lumen catheters 262, 264, and 266 have a body wall 268 with an exterior surface 270 and an interior surface 272, as well as a septum 274 that extends between spaced locations 276 and 278 on interior surface 272 to define two distinct longitudinally extending fluid flow lumens 280 and 282 within body wall 268.

First catheter 262 is, however, made of silicone, while second catheter 264 is made of polyurethane. Third catheter 266 can be made from either silicone or polyurethane. Each of lumens 280 and 282 of first catheter 262 and second catheter 264 have a substantially D-shaped transverse cross-section. In contrast, each of lumens 280 and 282 of third catheter 266 have a trapezoidal shaped transverse cross-section. Accordingly, each of the catheters 262, 264, and 266 have a combination of material composition and lumen configuration that is distinct from the other.

During use, prongs 50 and 52 of outlet stem 36 are received in individual of lumens 280 and 282 of select catheter 20 so that proximal end 254 of select catheter 20 is biased against sidewall 100 of barrel 102. In this position, as shown in FIG. 16, septum 274 is received in slot 81 between prongs 50 and 52.

Locking sleeve 260 is advanced over the portion of select catheter 20 on prongs 50 and 52. Locking sleeve 260 is positioned so that sidewall 100 of barrel 102 is received within recess 308, and locking ring 302 is positioned proximal of locking barb 92.

Locking sleeve 260 functions to form a sealed fluid coupling between prong 50 and lumen 282 and also between prong 52 and lumen 280. In part, this is accomplished by interior surface 298 of locking sleeve 260 compressing body wall 268 of catheter 20 against exterior surface 88 of outlet stem 36. More specifically, locking ring 302 compresses body wall 268 against outlet stem 36 at a position just proximal of locking barb 92. This interaction between exterior surface 88 of outlet stem 36 and body wall 208 of catheter 20 effects a sealed fluid communication therebetween.

Furthermore, the radial compressive force of locking ring 302 against prongs 50 and 52 wedges prongs 50 and 52 together at distal end 48. By compressing partition wall 274 between prongs 50 and 52, a fluid sealed is produced between partition wall 274 and inner face 90 of each of prongs 50 and 52.

The D-shaped configuration of each of prongs 50 and 52 enables each of catheters 262, 264, and 266 to be connected thereto in substantially the same way as shown above with regard to selected catheter 20, regardless of the cross sectional configuration of the lumens thereon.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed is:

1. An access port comprising:
   (a) a needle-impenetrable housing enclosing a plurality of discrete fluid reservoirs, each of said fluid reservoirs communicating with the exterior of said housing through a corresponding access aperture;
   (b) a needle-penetrable compound septum overlying said access apertures, said compound septum comprising:
      (i) a planar septum web having a top surface and a bottom surface; and
      (ii) a plurality of discrete plugs projecting from said bottom surface of said web, each of said plugs being received within a corresponding one of said access apertures of said fluid reservoirs; and
   (c) clamping means for securing said septum against said housing in sealing engagement with each of said access apertures.

2. An access port as recited in claim 1, further comprising a septum web recess in said housing that is configured to receive said septum web when each of said plugs are received within said corresponding one of said access apertures.

3. An access port as recited in claim 2, wherein said housing further comprising a top surface through which said discrete fluid reservoirs communicate with the exterior of said housing, and said septum web recess comprises:
   (a) a seat recessed within said top surface, said seat also defining each access aperture to said plurality of fluid reservoirs; and
   (b) an interior sidewall encircling said seat with a height extending between said seat and said top surface.

4. An access port as recited in claim 3, wherein said septum web has a side surface with a height extending between said top surface and said bottom surface of said septum web, said height of said side surface of said septum web being greater than said height of said interior sidewall of said septum web recess.

5. An access port as recited in claim 4, wherein said septum web has an outside perimeter defined by said side surface, and said septum web recess has an inside perimeter defined by said interior sidewall, said outside perimeter of said septum web being larger than said inside perimeter of said septum web recess, whereby said interior side wall of said septum web recess radially inwardly displaces said side surface of said septum web, when said septum web is received within said septum web recess.

6. An access port as recited in claim 1, wherein each of said plugs has an outside perimeter defined by a corresponding side surface, and each of said fluid reservoirs has an inside perimeter defined by said corresponding interior surfaces, said outside perimeter of each of said plugs being larger than said inside perimeter of each corresponding fluid reservoir, whereby said interior surface of each of said fluid reservoirs radially inwardly displaces said side surface of a corresponding one of said plugs, when said plugs are received within respective of said fluid reservoirs.

7. An access port as recited in claim 1, wherein said compound septum further comprises a plurality of discrete needle target domes on said top surface, each of said target domes being located opposite a corresponding one of said plugs.

8. An access port as recited in claim 1, wherein said compound septum is comprised of silicone.

9. An access port as recited in claim 1, wherein said access apertures are formed through a top surface of said housing, said housing includes a floor on the opposite side thereof from said top surface, and said clamping means comprises a shoe configured to receive said floor of said housing.

10. An access port as recited in claim 9, wherein said clamping means comprises a cap configured to receive said compound septum and said top surface of said housing and to engage said shoe, thereby compressing said septum against said top surface of said housing.

11. An access port as recited in claim 1, wherein said housing is made from a material selected from the group of materials consisting of metals, plastics, ceramics, and composites.

12. An access port as recited in claim 10, wherein said cap is made from a material selected from the group of materials consisting of metals, plastics, ceramics, and composites.

13. An access port comprising:
    (a) a housing having a floor and a top surface, said housing enclosing a plurality of discrete fluid reservoirs, each of said fluid reservoirs communicating with the exterior of said housing through a corresponding access aperture formed through said top surface of said housing;
    (b) delivery means for effecting fluid communication between each of said plurality of fluid reservoirs and the exterior of said housing;
    (c) a needle-penetrable compound septum overlying each of said access apertures;
    (d) a shoe configured to receive said floor of said housing; and
    (e) a cap configured to receive said compound septum and said top surface of said housing and to engage said shoe, thereby compressing said septum against said top surface of said housing.

14. An access port as recited in claim 13, wherein said shoe comprises:
    (a) annular ridge having an interior surface; and
    (b) an annular lip orthogonally projecting from said interior surface of said annular ridge.

15. An access port as recited in claim 13, wherein said cap comprises a sloping nose projecting from a proximal end thereof.

16. An access port as recited in claim 13, wherein said cap comprises a suture loop projecting therefrom.

17. An access port as recited in claim 13, wherein said compound septum comprises:
    (a) a septum web having a top surface, a bottom surface, and a side surface extending therebetween; and
    (b) a plurality of discrete plugs projecting from said bottom surface of said septum web and being individually received within a corresponding one of said access apertures of said fluid reservoirs.

18. An access port as recited in claim 17, wherein said compound septum further comprises a plurality of needle target domes on said top surface of said septum web.

19. An access port as recited in claim 18, wherein said cap comprises a plurality of apertures extending therethrough, individual of the needle target domes being received within a corresponding one of the apertures.

20. An access port as recited in claim 19, wherein said cap has an exterior surface with a tactile locating ridge projecting from said exterior surface between each of said plurality of apertures formed through said cap.

21. An access port as recited in claim 13, wherein said delivery means comprises a plurality of discrete fluid flow pathways, each individual fluid flow pathway extending between a corresponding one of said fluid reservoirs and a predetermined outlet location communicating with the exterior surface of the housing.

22. An access port as recited in claim 21, further comprising a stem projecting from the outlet location of the housing to a remote distal end, said stem comprising a plurality of fluid ducts extending from said distal end of said stem to a corresponding one of said fluid flow pathways.

23. An access port as recited in claim 13, wherein said cup is comprised of plastic.

24. An access port as recited in claim 13, wherein said housing is comprised of metal.

25. A dual reservoir access port comprising:
    (a) an elongated housing having proximal and distal ends and a top surface and a floor extending therebetween on opposite sides of said housing, said housing comprising:
        (i) a proximal fluid reservoir formed in said proximal end of said housing and communicating with the exterior of said housing through a proximal access aperture formed through said top surface of said housing;
        (ii) a distal fluid reservoir formed in said distal end of said housing and communicating with the exterior of said housing through a distal access aperture formed through said top surface of said housing;
        (iii) a first fluid flow pathway formed in said housing between a predetermined outlet location at said distal end of said housing and said proximal fluid reservoir; and
        (iv) a second fluid flow pathway formed in said housing between said predetermined outlet location and said distal fluid reservoir;
    (b) an outlet stem projecting from said housing at said outlet location with a distal end remote from said housing, said outlet stem comprising:
        (i) a first fluid duct longitudinally extending through said outlet stem between said distal end of said outlet stem and said first fluid flow pathway; and
        (ii) a second fluid duct longitudinally extending through said outlet stem between said distal end of said outlet stem and said second fluid flow pathway;
    (c) a needle-penetrable compound septum disposed against said top surface of said housing overlying said proximal access aperture and said distal access aperture; and
    (d) a clamp compressing said septum against said housing, said clamp comprising:
        (i) a cap configured to receive said top surface of said housing with said compound septum disposed thereagainst; and
        (ii) a shoe configured to receive said floor of said housing and to engage said cap.

26. A dual reservoir access port as recited in claim 25, wherein said clamp comprises a sloped nose projecting from a proximal end therefrom.

27. A dual reservoir access port as recited in claim 25, wherein said clamp comprises a suture loop projecting therefrom.

28. A dual reservoir access port as recited in claim 25, wherein said cap comprises a pair of apertures extending therethrough and a tactile locating ridge projecting from said cap between said pair of apertures.

29. A dual reservoir access port as recited in claim 25, wherein said clamp is comprised of plastic.

30. A dual reservoir access port as recited in claim 25, wherein said housing comprises a floor with a sidewall upstanding therefrom.

31. A dual reservoir access port as recited in claim 30, wherein said first fluid flow pathway is formed in said sidewall of said housing.

32. A dual reservoir access port as recited in claim 25, wherein said compound septum comprises:
   (a) a septum web having a top surface, a bottom surface, and a side surface extending therebetween; and
   (b) a pair of discrete plugs projecting from said bottom surface of said septum web and being individually received within said proximal access aperture and said distal access aperture.

33. An access port as recited in claim 32, further comprising a septum web recess in said housing that is configured to receive said septum web when each of said plugs are received within said corresponding one of said access apertures.

34. An access port as recited in claim 33, wherein said housing further comprising a top surface through which said access apertures communicate with the exterior of said housing, and said septum web recess comprises:
   (a) a seat recessed within said top surface, said seat also defining each access aperture to said plurality of fluid reservoirs; and
   (b) an interior sidewall encircling said seat with a height extending between said seat and said top surface.

35. An access port as recited in claim 34, wherein said septum web has a side surface with a height extending between said top surface and said bottom surface, said height of said side surface being greater than said height of said interior sidewall of said septum web recess.

36. A dual reservoir access port as recited in claim 32, wherein said septum further comprises a pair of needle target domes projecting from said top surface of said septum web.

37. An implantable fluid delivery system comprising:
   (a) an implantable dual reservoir access port comprising:
      (i) a housing having a proximal end and a distal end, said housing comprising:
         (A) a proximal fluid reservoir formed in said proximal end of said housing and communicating with the exterior of said housing through a proximal access aperture;
         (B) a distal fluid reservoir formed in said distal end of said housing and communicating with the exterior of said housing through a distal access aperture;
         (C) a first fluid flow pathway formed in said housing between a predetermined outlet location at said distal end of said housing and said proximal fluid reservoir; and
         (D) a second fluid flow pathway formed in said housing between said predetermined outlet location and said distal fluid reservoir;
      (ii) an outlet stem projecting from said housing at said outlet location with a distal end remote from said housing, said outlet stem comprising:
         (A) a first and a second outlet prong at said distal end of said outlet stem, each of said first and second outlet prongs having an exterior surface and an opposing inner face, said opposing inner faces defining a slot in said distal end of said outlet stem;
         (B) a first fluid duct longitudinally extending through said first outlet prong of said outlet stem to said first fluid flow pathway; and
         (C) a second fluid duct longitudinally extending through said second outlet prong of said outlet stem to said second fluid flow pathway;
      (iii) a needle-penetrable compound septum overlying said proximal access aperture and said distal access aperture;
      (iv) a clamp configured to compress said septum to said housing, said clamp comprising:
         (A) a shoe configured to receive said floor of said housing; and
         (B) a cap configured to receive said compound septum and said top surface of said housing and to engage said shoe, thereby compressing said septum against said housing;
   (b) a dual lumen catheter comprising a body wall enclosing a pair of longitudinally extending fluid flow lumens separated by a septum; and
   (c) a locking sleeve having a proximal end, a distal end, and an interior surface defining a passageway longitudinally extending through said locking sleeve, said interior surface of said locking sleeve radially, inwardly compressing a portion of said body wall of said dual lumen catheter against a portion of said exterior surface of said stem, when said distal end of each of said first and second outlet prongs is individually received in a corresponding one of said lumens of said dual lumen catheter and said dual lumen catheter with said stem received therein is positioned within said passageway of said locking sleeve.

38. An implantable fluid delivery system as recited in claim 37, wherein said housing further comprises a floor with a sidewall upstanding therefrom.

39. An implantable fluid delivery system as recited in claim 38, wherein said first fluid flow pathway is formed in said sidewall of said housing.

40. An implantable fluid delivery system as recited in claim 37, wherein said compound septum comprises:
   (a) a planar septum web having a top surface, a bottom surface, and a side surface extending therebetween; and
   (b) a pair of discrete plugs projecting from said bottom surface of said septum web and being individually received within said proximal access aperture and said distal access aperture.

41. An implantable fluid delivery system as recited in claim 37, further comprising a tactile locating ridge projecting from said cap.

42. An implantable fluid delivery system as recited in claim 37, further comprising a sloping nose projecting from a proximal end of said clamp.

43. An implantable fluid delivery system as recited in claim 37, wherein said dual lumen catheter is comprised of silicone and said interior surface of each of said lumens are substantially D-shaped.

44. An implantable fluid delivery system as recited in claim 37, wherein said dual lumen catheter is comprised of polyurethane and said interior surface of each of said lumens are substantially D-shaped.

45. An implantable fluid delivery system as recited in claim 37, wherein said a dual lumen catheter is comprised of silicone and said interior surface of each of said lumens are substantially trapezoidal shaped.

46. An implantable fluid delivery system as recited in claim 37, wherein said interior surface of said locking sleeve comprises a substantially cylindrical locking ring.

47. An implantable fluid delivery system as recited in claim 46, wherein each of said first and second outlet prongs has a locking barb radially projecting out from said exterior surface thereof, and wherein said locking ring is positioned so as to be located proximal of said locking barbs when said distal end of each of said outlet prongs is individually received in individual lumens of said dual lumen catheter and said dual lumen catheter with said stem received therein is positioned within said passageway of said locking sleeve.

48. An implantable fluid delivery system as recited in claim 46, wherein said interior surface of said locking sleeve further comprises a frustoconical first portion radially sloping outward from said locking ring to said proximal end of said locking sleeve.

49. An implantable fluid delivery system as recited in claim 46, further comprising a frustoconical second portion radially sloping outward from said locking ring to said distal end of said locking sleeve.

50. An implantable fluid delivery system as recited in claim 37, wherein said locking sleeve comprises a die notch formed at said distal end of said exterior surface of said locking sleeve.

51. An implantable fluid delivery system as recited in claim 37, wherein said locking sleeve further comprises gripping means for increasing frictional engagement with said exterior surface of said locking sleeve.

52. An implantable fluid delivery system as recited in claim 51, wherein said gripping means comprises an annular bias ring encircling and radially extending out from said exterior surface of said locking sleeve.

53. A subassembly for a dual reservoir access port, the subassembly comprising:
   (a) a housing comprising a floor and an encircling sidewall upstanding therefrom, said housing further comprising:
      (i) a proximal fluid reservoir interior of said sidewall at a proximal end of said housing;
      (ii) a distal fluid reservoir interior of said sidewall at a distal end of said housing; and
      (iii) a fluid flow pathway formed in said sidewall of said housing between said proximal fluid reservoir and the exterior of said housing at a predetermined outlet location at said distal end of said housing; and
   (b) an outlet stem projecting from said housing at said outlet location with a distal end remote from said housing, said outlet stem comprising:
      (i) a first fluid duct longitudinally extending through said outlet stem between said distal end of said outlet stem and said fluid flow pathway; and
      (ii) a second fluid duct longitudinally extending through said outlet stem between said distal end of said outlet stem and said distal fluid reservoir.

54. A subassembly as recited in claim 53, further comprising a dividing wall separating said distal fluid reservoir from said proximal fluid reservoir.

55. A subassembly as recited in claim 53, further comprising an outlet port formed at said outlet location with said outlet stem received therein, said outlet port extending between the exterior of said housing and said fluid flow pathway.

56. A subassembly as recited in claim 55, further comprising:
   (a) an entry port formed in said housing from said fluid flow pathway to said distal fluid reservoir, said entry port being substantially aligned with said outlet port; and
   (b) a boss projecting from a proximal end of said outlet stem with said second fluid duct extending therethrough, said boss being received within said entry port when said proximal end of said stem is received within said outlet port.

57. A subassembly as recited in claim 53, wherein said housing comprises:
   (a) a passageway extending through said housing at said distal end of said housing; and
   (b) an open basket having an exterior surface received within said aperture, said open basket having interior surface defining said distal fluid reservoir.

58. A subassembly as recited in claim 53, wherein said housing further comprises:
   (a) a distal cup formed at said distal end of said housing with an interior surface; and
   (b) a sleeve received within said distal cup, said sleeve comprising:
      (i) an exterior surface mounted on a portion of said interior surface of said distal cup; and
      (ii) an interior surface, said interior surface of said sleeve and said interior surface of said distal cup not having said sleeve mounted thereon defining said distal fluid reservoir.

59. A subassembly as recited in claim 58, wherein said sleeve is substantially C-shaped.

60. A subassembly as recited in claim 58, wherein said sleeve has the configuration of a continuous ring.

61. A subassembly as recited in claim 53, wherein said housing comprises:
   (a) a distal cup formed at said distal end of said housing with an interior surface; and
   (b) an open-topped basket having an exterior surface configured to be received within said distal cup, said basket also having an interior surface defining said distal fluid reservoir.

62. A subassembly as recited in claim 61, further comprises:
   (a) an outlet port formed at said outlet location, said outlet port extending between the exterior of the housing and said distal cup;
   (b) an entry port extending between said interior surface and said exterior surface of said open-topped basket, said entry port being substantially aligned with said outlet port; and
   (c) a boss projecting from a proximal end of said outlet stem with said second fluid duct extending therethrough, said boss being received within said entry port when said proximal end of said stem is received within said outlet port.

63. A subassembly as recited in claim 53, wherein said housing is comprised of metal.

64. A subassembly as recited in claim 53, wherein said housing is comprised of plastic.

65. A subassembly as recited in claim 53, wherein said housing is comprised of ceramic.

66. A subassembly as recited in claim 53, wherein said outlet stem comprises a pair of parallel, spaced-apart outlet prongs at said distal end of said outlet stem.

67. A subassembly as recited in claim 53, wherein in a transverse cross section of said stem, said first fluid duct at said distal end of said outlet stem is substantially D-shaped.

68. A subassembly as recited in claim 53, wherein in a transverse cross section of said stem, said first fluid duct at said proximal end of said outlet stem is substantially circular shaped.

69. A subassembly for a dual reservoir access port, the subassembly comprising:
   (a) a casing having a proximal fluid reservoir formed in a proximal end of said casing and a distal cup formed in a distal end of said casing;

(b) a sleeve received in said distal cup with an exterior surface of said sleeve engaging a portion of the interior surface of said distal cup;

(c) an outlet stem projecting from said casing at a predetermined outlet location at said distal end of said casing with a free distal end remote from said casing, said outlet stem comprising:

(i) a first fluid duct longitudinally extending from said distal end of said stem to said casing; and (ii) a second fluid duct longitudinally extending from said distal end of said stem to said distal cup; and (d) fluid conduit means between said casing and said sleeve for placing said proximal fluid reservoir in fluid communication with said first fluid duct of said outlet stem.

70. A subassembly as recited in claim 69, wherein said sleeve is substantially C-shaped.

71. A subassembly as recited in claim 69, wherein said sleeve comprises a continuous cylindrical ring.

72. A subassembly as recited in claim 71, wherein said subassembly further comprises a base attached to said sleeve to form an open-topped basket, said open-topped basket having an interior surface defining said distal fluid reservoir.

73. A subassembly as recited in claim 69, wherein said fluid conduit means comprises:

(a) a channel recessed in said interior surface of said distal cup and extending from said distal end of said casing to said dividing wall;

(b) an outlet port extending through said casing from said distal end of said casing to said channel; and (c) a transfer port extending through said dividing wall from said proximal fluid reservoir to said channel.

74. A subassembly as recited in claim 69, wherein said fluid conduit means comprises:

(a) a channel recessed in said exterior surface of said sleeve and extending from said distal end of said casing to said dividing wall;

(b) an outlet port extending through said casing from said distal end of said casing to said channel; and (c) a transfer port extending through said dividing wall from said proximal fluid reservoir to said channel.

75. A subassembly as recited in claim 73, further comprising:

(a) an entry port formed in said sleeve, said entry port being substantially aligned with said outlet port; and (b) a boss projecting from said proximal end of said outlet stem and having said second fluid duct extending therethrough, said boss being received within said entry port when said proximal end of said stem is received within said outlet port.

76. A subassembly as recited in claim 69, wherein said outlet stem further comprises a pair of outlet prongs formed at said distal end of said outlet stem.

77. A subassembly as recited in claim 69, wherein said casing is comprised of metal.

78. A subassembly as recited in claim 69, wherein said sleeve is comprised of metal.

79. A subassembly for a dual reservoir access port, the subassembly comprising:

(a) a casing having a proximal fluid reservoir formed in a proximal end of said casing and a distal cup formed in said distal end of said casing;

(b) an open-topped basket defining a distal fluid reservoir received in said distal cup, said basket having an exterior surface engaging a predetermined portion of an interior surface of said distal cup;

(c) a fluid flow pathway located between said basket and said distal cup, said fluid flow pathway extending from said proximal fluid reservoir to the exterior of said casing at a predetermined outlet location at said distal end of said casing; and (d) an outlet stem projecting from said casing at said outlet location with a distal end remote from said casing, said outlet stem comprising:

(i) a first fluid duct longitudinally extending through said outlet stem between said distal end of said outlet stem and said fluid flow pathway; and (ii) a second fluid duct longitudinally extending through said outlet stem between said distal end of said outlet stem and said distal fluid reservoir.

80. A subassembly as recited in claim 79, wherein said casing comprises a floor with an encircling sidewall upstanding therefrom.

81. A subassembly as recited in claim 79, wherein said fluid flow pathway is formed in said sidewall of said casing.

82. A subassembly as recited in claim 79, wherein said fluid flow pathway comprises a channel recessed in said exterior surface of said open-topped basket.

83. A subassembly as recited in claim 79, wherein said basket comprises:

(a) a base having an outside perimeter; and (b) a cylindrical sleeve orthogonally projecting from said outside perimeter of said base.

84. A subassembly as recited in claim 79, further comprising:

(a) an outlet port at said outlet location, said outlet port extending between the exterior of said casing and said distal cup;

(b) an entry port formed in said basket, said entry port being substantially aligned with said outlet port; and (c) a boss projecting from said proximal end of said outlet stem and having said second fluid duct extending therethrough, said boss being received within said entry port when a proximal end of said stem is received within said outlet port.

85. A subassembly as recited in claim 79, further comprising a pair of outlet prongs formed at said distal end of said stem, said first fluid duct and said second fluid duct being individually disposed within a corresponding one of said outlet prongs.

86. A subassembly as recited in claim 85, wherein each of said outlet prongs has an exterior surface and an inner face, opposing inner faces defining a slot in said outlet stem.

87. A subassembly as recited in claim 86, wherein said outlet stem further comprises a locking barb, radially outwardly extending on each exterior surface of each outlet prong.

88. A subassembly as recited in claim 79, wherein said outlet stem is comprised of metal.

89. An outlet stem for an access port, the outlet stem comprising:

(a) an exterior surface extending between a proximal end and a distal end; and (b) an interior surface defining a first fluid duct longitudinally extending between said distal end and said proximal end, said first fluid duct at said distal end of said outlet stem having a substantially D-shaped transverse cross-section, and said first fluid duct at said proximal end of said outlet stem having a substantially circular shaped transverse cross-section.

90. An outlet stem as recited in claim 89, wherein said cross-sectional shape of said first fluid duct smoothly and continuously changes between said proximal end of said outlet stem and said distal end of said outlet stem.

91. An outlet stem as recited in claim 89, wherein said outlet stem further comprises a second fluid duct adjacent to said first fluid duct and extending between said proximal end and said distal end of said outlet stem.

92. An outlet stem as recited in claim 91, further comprising a boss projecting from said proximal end of said stem with said second fluid duct extending therethrough.

93. An outlet stem as recited in claim 92, wherein said boss has a substantially cylindrical configuration.

94. An outlet stem as recited in claim 91, further comprising a slot longitudinally extending between the first fluid duct and the second fluid duct at said distal end of said stem.

95. An outlet stem as recited in claim 89, further comprising a locking barb radially outwardly extending on said exterior surface of said stem at said distal end of said stem.

96. An outlet stem as recited in claim 89, wherein said outlet stem is comprised of metal.

97. An outlet stem for a dual reservoir access port, the outlet stem comprising:
(a) a stem barrel having a proximal end and a distal end;
(b) first and second parallel outlet prongs projecting from said distal end of said stem barrel and each terminating in a respective free end;
(c) a boss projecting from a portion of said proximal end of said stem barrel;
(d) a first fluid duct longitudinally extending through said first outlet prong, said stem barrel, and said boss, said first fluid duct having a transverse cross section at one end thereof distinct from the transverse cross section at the other end thereof; and
(e) a second fluid duct extending longitudinally through said second outlet prong and said stem barrel, said second fluid duct having a transverse cross section at one end thereof distinct from the transverse cross section at the other end thereof.

98. An outlet stem as recited in claim 97, wherein the end of said first fluid duct at said free end of said first prong has a substantially D-shaped transverse cross section.

99. An outlet stem as recited in claim 97, wherein the end of said first fluid duct at said boss has a substantially circular transverse cross section.

100. An outlet stem as recited in claim 97, wherein the end of said second fluid duct at said proximal end of said stem barrel has a substantially circular transverse cross section.

101. An outlet stem as recited in claim 97, wherein the transverse cross section of said first fluid duct transitions smoothly and continuously between said ends thereof.

102. An outlet stem as recited in claim 97, wherein each of said outlet prongs has an exterior surface and an inner face, and said inner faces of said outlet prongs are disposed in parallel opposed relation to define a slot in said outlet stem.

103. An outlet stem as recited in claim 102, wherein said outlet stem further comprises a locking barb radially, outwardly extending on said exterior surface of each of said outlet prongs.

104. An outlet stem as recited in claim 97, wherein said boss has a substantially cylindrical configuration.

105. A method of manufacturing an outlet stem for an implantable access port, the method comprising the steps of:
(a) providing a stem body having a distal end face, a proximal end face, and an encircling exterior surface extending therebetween;
(b) forming a pilot passageway through said stem body from said distal end face to said proximal end face;
(c) disposing an EDM wire though said pilot passageway; and
(d) enlarging said pilot passageway by removing portions of the stem body adjacent to said pilot passageway with said EDM wire, thereby forming a fluid duct having distinct transverse cross sections at the opposite ends thereof.

106. A method as recited in claim 105, wherein said EDM wire comprises a distal end positioned exterior of said distal end face of said stem body after said step of disposing, and said step of enlarging comprises the step of moving said distal end of said EDM wire to produce a substantially D-shaped transverse cross section in said fluid duct at said distal end of said stem.

107. A method as recited in claim 105, wherein said EDM wire comprises a proximal end positioned exterior of said proximal face of said stem body after said step of disposing, and wherein said step of enlarging comprises the step of moving said proximal end of said EDM wire to produce a substantially circular transverse cross section in said fluid duct at said proximal end of said stem.

108. A method as recited in claim 105, wherein said step of forming comprises the steps of:
(a) drilling a first pilot hole in said proximal end face of said stem; and
(b) drilling a second pilot hole in said distal end face of said stem a sufficient distance to intersect said first pilot hole.

109. A method as recited in claim 108, wherein the diameter of said first pilot hole is larger than the diameter of said second pilot hole.

110. A method as recited in claim 105, further comprising the steps of:
(a) cutting an encircling groove in said exterior surface of said stem body at a location between said proximal end and said distal end of said stem body; and
(b) tapering said stem body at said distal end thereof, thereby forming a barb encircling of said outlet stem and flaring radially outwardly from said distal end of said stem body toward said groove.

111. A method as recited in claim 105, further comprising the step of forming a longitudinally extending slot from said distal end face of said stem body into said body stem, thereby forming a pair of prongs at said distal end of said stem body on opposite sides of said slot.

112. A method of manufacturing a dual reservoir access port, the method comprising the steps of:
(a) forming in a needle-impenetrable casing a distal cup, an open-topped proximal fluid reservoir, and a fluid flow pathway extending between said proximal fluid reservoir and a predetermined outlet location on the opposite side of said distal cup from said proximal fluid reservoir;
(b) positioning an open-topped basket in said distal cup, thereby defining an open-topped distal fluid reservoir within said basket;
(c) fabricating an outlet stem enclosing first and second fluid ducts longitudinally extending therethrough;
(d) securing the proximal end of said outlet stem to said casing at said predetermined outlet location with said first fluid duct communicating with said fluid flow pathway and said second fluid duct communicating with said distal fluid reservoir;
(e) covering the top of said distal fluid reservoir and the top of said proximal fluid reservoir with a needle-penetrable compound septum; and (f) clamping said compound septum against said casing to preclude fluid communication between said proximal fluid reservoir and said distal fluid reservoir.

113. A method as recited in claim 112, wherein said step of positioning comprises the steps of:

(a) inserting said basket in said distal cup; and (b) welding a top edge of said basket to said casing.

114. A method as recited in claim 112, wherein said compound septum comprises a septum web and a pair of septum plugs projecting from the same side thereof, and said step of covering comprising the step of inserting individual of said septum plugs into corresponding of said proximal fluid reservoirs and said distal fluid reservoir, respectively.

115. A method as recited in claim 112, wherein said step of clamping comprises the steps of:

(a) compressing said septum against said housing between a cap and a shoe; and (b) securing said cap to said shoe.

116. A septum for use in an implantable dual reservoir vascular access port of the type having a needle-impenetrable housing enclosing distinct first and second fluid reservoirs accessible from the exterior of the access port through corresponding first and second access apertures formed through a wall of the housing, said septum comprising:

(a) a septum web having a top surface, a bottom surface, and a surrounding side surface therebetween;

(b) a first septum plug projecting from said bottom surface of said web; and (c) a second septum pug distinct from said first septum plug projecting from said bottom surface of said web.

117. A septum as recited in claim 116, wherein said septum web is generally planar.

118. A septum as recited in claim 116, further comprising:

(a) a first needle target dome projecting from said top surface of said septum web opposite said first septum plug; and (b) a second needle target dome projecting from said top surface of said septum web opposite said second septum plug.

119. A septum as recited in claim 116, wherein said septum is comprised of silicone.

120. A septum as recited in claim 117, wherein in a cross section of said septum web taken in the plane thereof said side surface of said septum web assumes the shape of a figure eight.

* * * * *